US012661273B2

(12) United States Patent
Quintero et al.

(10) Patent No.: US 12,661,273 B2
(45) Date of Patent: Jun. 23, 2026

(54) WOUND CLOSURE SYSTEM HAVING MICROCANNULAIC PATHWAYS

(71) Applicant: Cilag GmbH International, Zug (CH)

(72) Inventors: Julian A. Quintero, Flemington, NJ (US); Leo B. Kriksunov, Ithaca, NY (US); Robert J. Tannhauser, Bridgewater, NJ (US)

(73) Assignee: Cilag GmbH International, Zug (CH)

( * ) Notice: Subject to any disclaimer, the term of this patent is extended or adjusted under 35 U.S.C. 154(b) by 646 days.

(21) Appl. No.: 17/991,950

(22) Filed: Nov. 22, 2022

(65) Prior Publication Data

US 2024/0164950 A1     May 23, 2024

(51) Int. Cl.
| | |
|---|---|
| *A61F 13/0246* | (2024.01) |
| *A61F 13/00* | (2024.01) |
| *A61F 13/0206* | (2024.01) |
| *A61M 1/00* | (2006.01) |

(52) U.S. Cl.
CPC ...... *A61F 13/025* (2013.01); *A61F 13/00063* (2013.01); *A61F 13/0206* (2013.01); *A61M 1/85* (2021.05)

(58) Field of Classification Search
CPC .............. A61F 13/025; A61F 13/00063; A61F 13/0206; A61F 13/0203; A61F 13/05; A61M 1/85; A61M 1/915; A61M 1/92; A61M 1/912; A61M 1/913
See application file for complete search history.

(56) References Cited

U.S. PATENT DOCUMENTS

| | | | | |
|---|---|---|---|---|
| 4,899,739 | A | * | 2/1990 | Konishi ................. A61L 15/58 604/306 |
| 8,057,446 | B2 | | 11/2011 | Kane et al. |
| 8,246,590 | B2 | | 8/2012 | Hu et al. |
| 9,173,777 | B2 | | 11/2015 | Zurovcik |
| 10,105,265 | B2 | | 10/2018 | Niederauer et al. |
| 10,357,404 | B2 | | 7/2019 | Lockwood et al. |
| 10,792,024 | B2 | | 10/2020 | Quintero et al. |
| 11,058,807 | B2 | | 7/2021 | Weston |
| 11,160,917 | B2 | | 11/2021 | Shuler |

(Continued)

OTHER PUBLICATIONS

U.S. Appl. No. 17/991,945, filed Nov. 22, 2022, by Quintero et al., entitled: "Surgical Mesh Securing Device for Wound Closure System."

(Continued)

*Primary Examiner* — Guy K Townsend
*Assistant Examiner* — Alessandro R Del Priore
(74) *Attorney, Agent, or Firm* — Amir Bishara

(57) ABSTRACT

An apparatus includes a cannula that can establish fluid communication with a suction source, and a wound closure path dimensioned to cover a wound in skin. The wound closure patch can receive a topical adhesive to adhere to the skin and form a microbial barrier over the wound. The wound closure patch defines a channel. The wound closure patch includes a top surface, a bottom surface defining at least one channel interposed between the top surface and the bottom surface, and a fluid coupling section in fluid communication with the channel. The fluid coupling section can couple with the cannula to thereby establish fluid communication between the cannula, the channel, and the at least one opening defined by the bottom surface.

20 Claims, 19 Drawing Sheets

(56) References Cited

U.S. PATENT DOCUMENTS

| | | | |
|---|---|---|---|
| 11,479,669 | B2 | 10/2022 | Ou |
| 11,518,604 | B2 | 12/2022 | Ou et al. |
| 11,589,867 | B2 | 2/2023 | Ou et al. |
| 11,596,555 | B2 | 3/2023 | Dutta et al. |
| 11,638,666 | B2 | 5/2023 | Hartwell et al. |
| 11,712,229 | B2 | 8/2023 | Ou et al. |
| 2002/0161346 | A1 * | 10/2002 | Lockwood .............. A61M 1/92 |
| | | | 604/315 |
| 2014/0128824 | A1 | 5/2014 | Croizat et al. |
| 2017/0189237 | A1 * | 7/2017 | Locke ..................... A61F 13/05 |
| 2018/0010025 | A1 * | 1/2018 | Hartwell ................ C09J 201/02 |
| 2018/0085103 | A1 * | 3/2018 | Quintero .............. A61L 24/046 |
| 2021/0106737 | A1 | 4/2021 | Obst et al. |
| 2021/0161723 | A1 | 6/2021 | Blurton et al. |
| 2021/0169700 | A1 | 6/2021 | Hill et al. |
| 2021/0369639 | A1 | 12/2021 | Ou |
| 2022/0395643 | A1 | 12/2022 | Ou et al. |
| 2024/0000455 | A1 | 1/2024 | Bick et al. |
| 2024/0074911 | A1 | 3/2024 | Madriz et al. |

OTHER PUBLICATIONS

U.S. Appl. No. 17/991,992, filed Nov. 22, 2022, by Ou et al., entitled: "Application of Topical Skin Adhesive to Surgical Mesh."
U.S. Appl. No. 63/427,132, filed Nov. 22, 2022, by Perkins et al., entitled: "Device for Spreading Topical Skin Adhesive."
International Search Report and Written Opinion dated Feb. 7, 2024, for International Application No. PCT/IB2023/061722, 16 pages.

* cited by examiner

WOUND CLOSURE SYSTEM HAVING MICROCANNULAIC PATHWAYS

BACKGROUND

A wound closure system (also referred to as a skin closure system) may be used at the conclusion of a surgical procedure on a patient to close a wound (e.g., a surgical incision) that was formed in the patient's skin for accessing a target anatomical structure. By way of example, wound closure systems may include components such as sutures, substrates, and/or liquid topical skin adhesives that are applied by a surgeon to approximate the edges of the wound and, in some cases, form a stable and protective layer over the wound that promotes efficient healing. In some instances, one or more components of the applied wound closure system may be absorbed by the patient during the healing process. Following healing of the wound, remaining components of the wound closure system may be removed from the skin by a surgeon, and/or they may automatically separate from the skin such that they may be discarded by the patient.

While various wound closure systems and associated components and methods have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the description given below, serve to explain the principles of the present invention.

Figure 1:
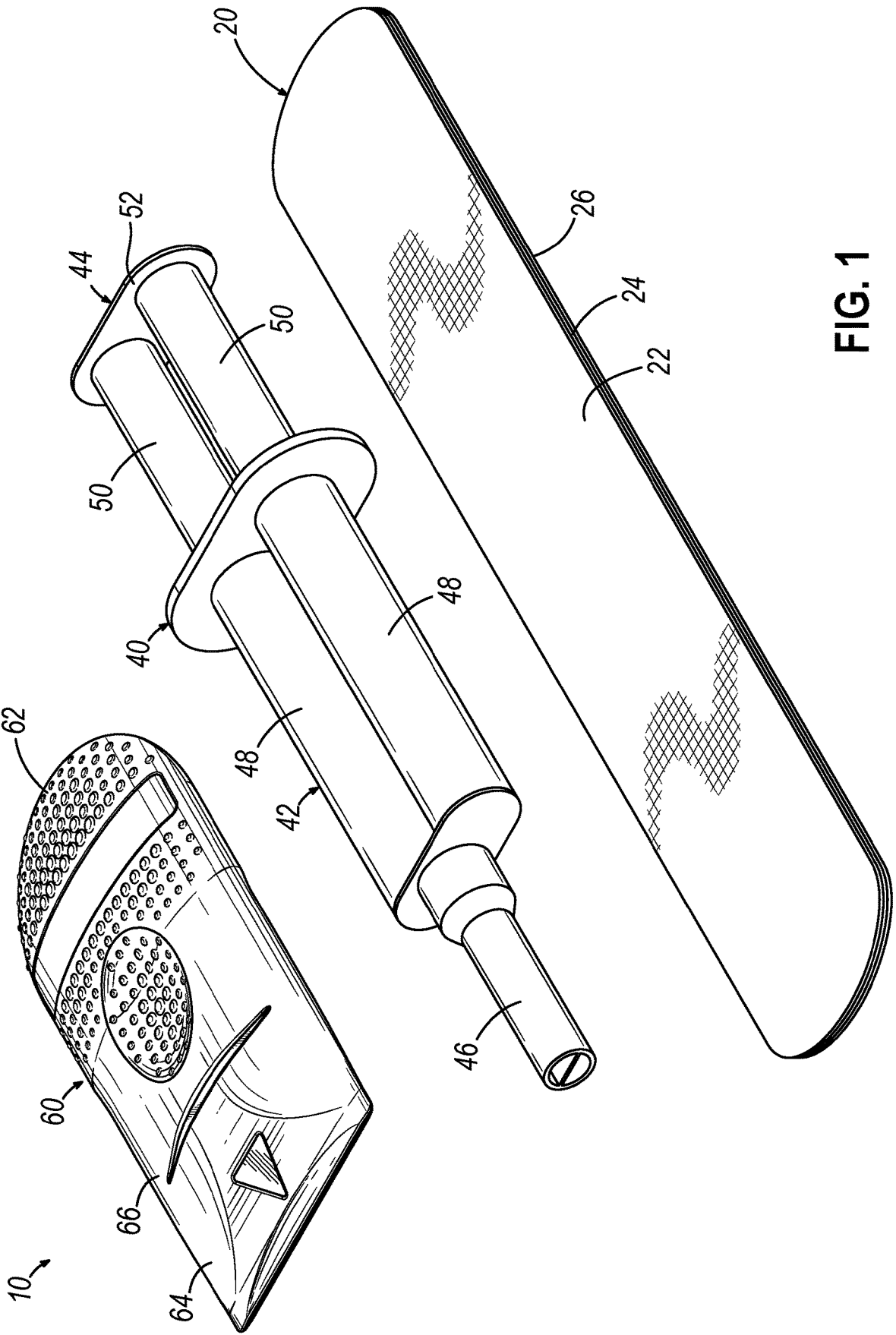
FIG. 1 depicts a perspective view of an example of a wound closure system that includes a wound closure device, an adhesive applicator, and an adhesive spreader.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "side," "upwardly," and "downwardly" also are used herein for reference to relative positions and directions. Such terms are used below with reference to views as illustrated for clarity and are not intended to limit the invention described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Wound Closure System

FIG. 1 shows an example of a wound closure system (10) that includes a wound closure device (20) (also referred to as a patch) configured to be applied to a patient's wound (W), an adhesive applicator (40) configured to apply a topical skin adhesive (54) (see FIG. 3D) to the applied wound closure device (20), and an adhesive spreader (60) configured to spread the applied topical skin adhesive (54) onto and through wound closure device (20). Each of these components is described in greater detail below.

Figure 2:
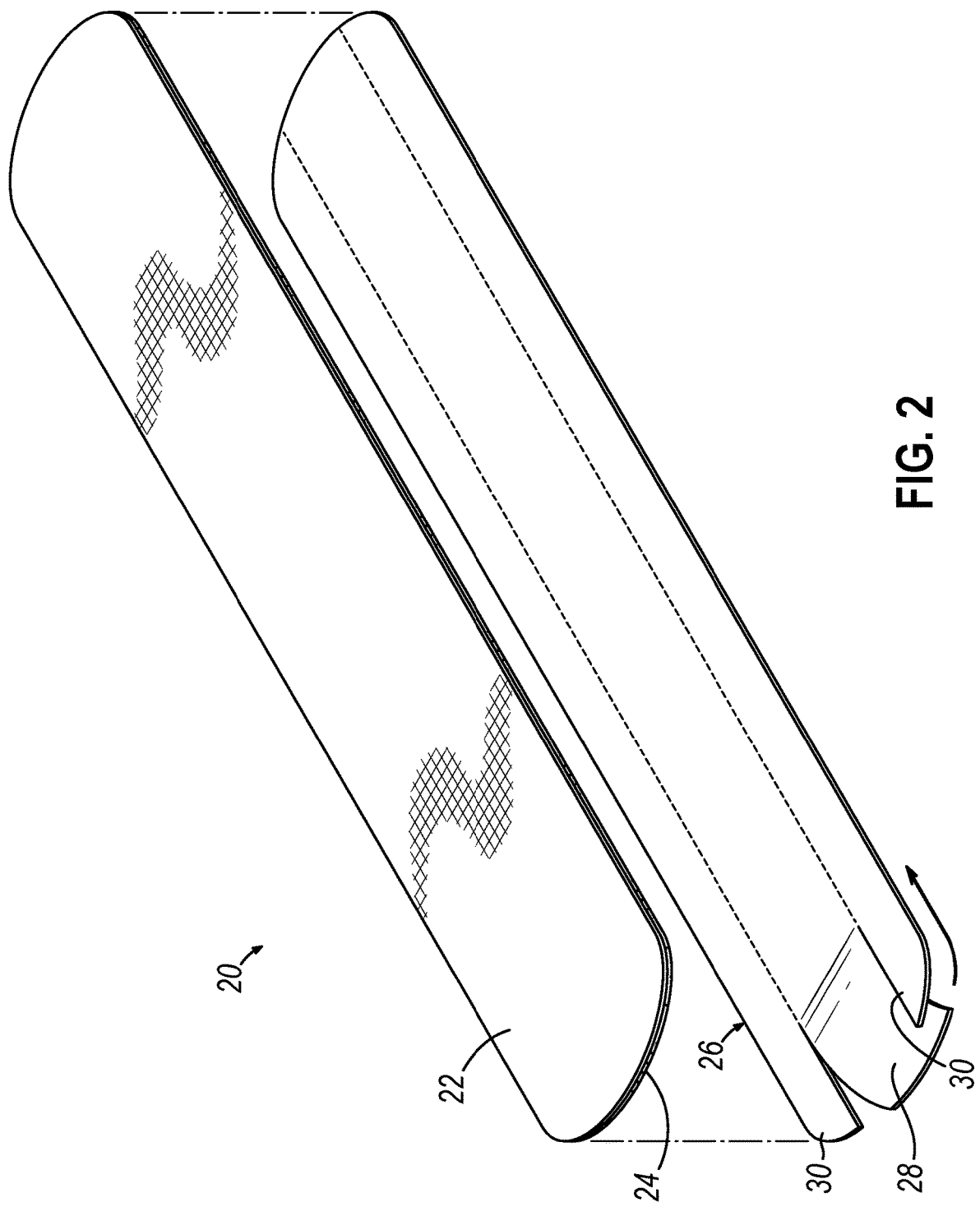
FIG. 2 depicts a disassembled perspective view of the wound closure device of FIG. 1, showing a mesh layer, a pressure sensitive adhesive layer, and a removable backing layer.

As shown best in FIG. 2, wound closure device (20) of the present version has an elongate, generally rectangular shape and a triple layer construction. More specifically, wound closure device (20) includes a layer of substrate in the form of a textile mesh (22), a layer of pressure sensitive adhesive (24) formed as a continuous or non-continuous coating along the lower skin-facing side of mesh (22), and a layer of backing (26) removably applied to the lower side of pressure sensitive adhesive (24). It will be understood that the term "wound closure device" as used herein encompasses wound closure device (20) both with and without backing (26), which may be removed and discarded during application of wound closure device (20) to a patient, as described in greater detail below.

Mesh (22) is configured to retain a liquid topical skin adhesive and may be formed of polyethylene (PET) or any other suitable surgical textile material. Pressure sensitive adhesive (24) is configured to enable wound closure device (20) to self-adhere to a patient's skin in response to a pressure being applied to the upper side of mesh (22) during its application by a surgeon. Backing (26) serves to protect pressure sensitive adhesive (24) before application of wound closure device (20) to the patient. In the present version, backing (26) includes elongate arrays of perforations that extend longitudinally and define an elongate central backing section (28) and a pair of elongate side backing sections (30). Though each backing section (28, 30) is shown as generally rectangular in the present version, backing sections (28, 30) may be of various alternative shapes, sizes, and quantities in other versions.

As shown in FIG. 1, adhesive applicator (40) includes an applicator body (42), a plunger unit (44) slidably received within an open proximal end of applicator body (42), and a static mixer (46) secured to a distal end of applicator body (42). Applicator body (42) includes a pair of barrels (48) arranged side by side, where each barrel (48) houses a respective part of a two-part liquid topical skin adhesive. Plunger unit (44) includes a pair of plungers (50) that are arranged side by side and are interconnected at their proximal ends by a bridge (52). Each plunger (50) is actuatable distally through a respective barrel (48) of applicator body (42) to force the corresponding liquid adhesive part distally into static mixer (46). Static mixer (46) is configured to receive the first and second adhesive parts and direct them around and through a series of static baffles and passages (not shown) that mix the two adhesive parts together into a homogenous liquid adhesive (54) that is then dispensed through an open distal end of static mixer (46), as shown in FIG. 3D described below.

In the present version, liquid topical skin adhesive (54) is in the form of a silicone-based topical skin adhesive that is configured to cure on skin at body temperature in less than two minutes. Once cured, topical skin adhesive (54) remains elastomeric such that a given section of cured adhesive (54) is configured to stretch up to 160% of its cured length and then fully recover to the cured length. Accordingly, wound closure system (10) may be particularly effective for use on actuatable body parts of a patient such as a knee, wrist, elbow, or other joint, for example.

As also shown in FIG. 1, adhesive spreader (60) of the present version has a monolithic body that includes a proximal body portion (62) configured to be gripped by a user, a distal body portion (64) that terminates at a tip configured to spread applied topical skin adhesive (54), and an intermediate flexural body portion (66) that interconnects the proximal and distal body portions (62, 64). Flexural body portion (66) is configured to elastically deform so that distal body portion (64) angularly deflects relative to proximal body portion (62) to promote effective spreading of topical skin adhesive (54) along wound closure device (20) with a suitable normal force within a predetermined range.

FIGS. 3A-3D show an example of wound closure system (10) being used to close a wound (W) formed in the skin (S) of a patient. In some procedures, wound (W) may be at least partially closed with one or more sutures, for example at deeper portions of wound (W), prior to use of wound closure system (10). Additionally, before wound closure device (20)

is applied to the patient, it may be trimmed by a surgeon to any suitable shape as desired.

Figure 3A:
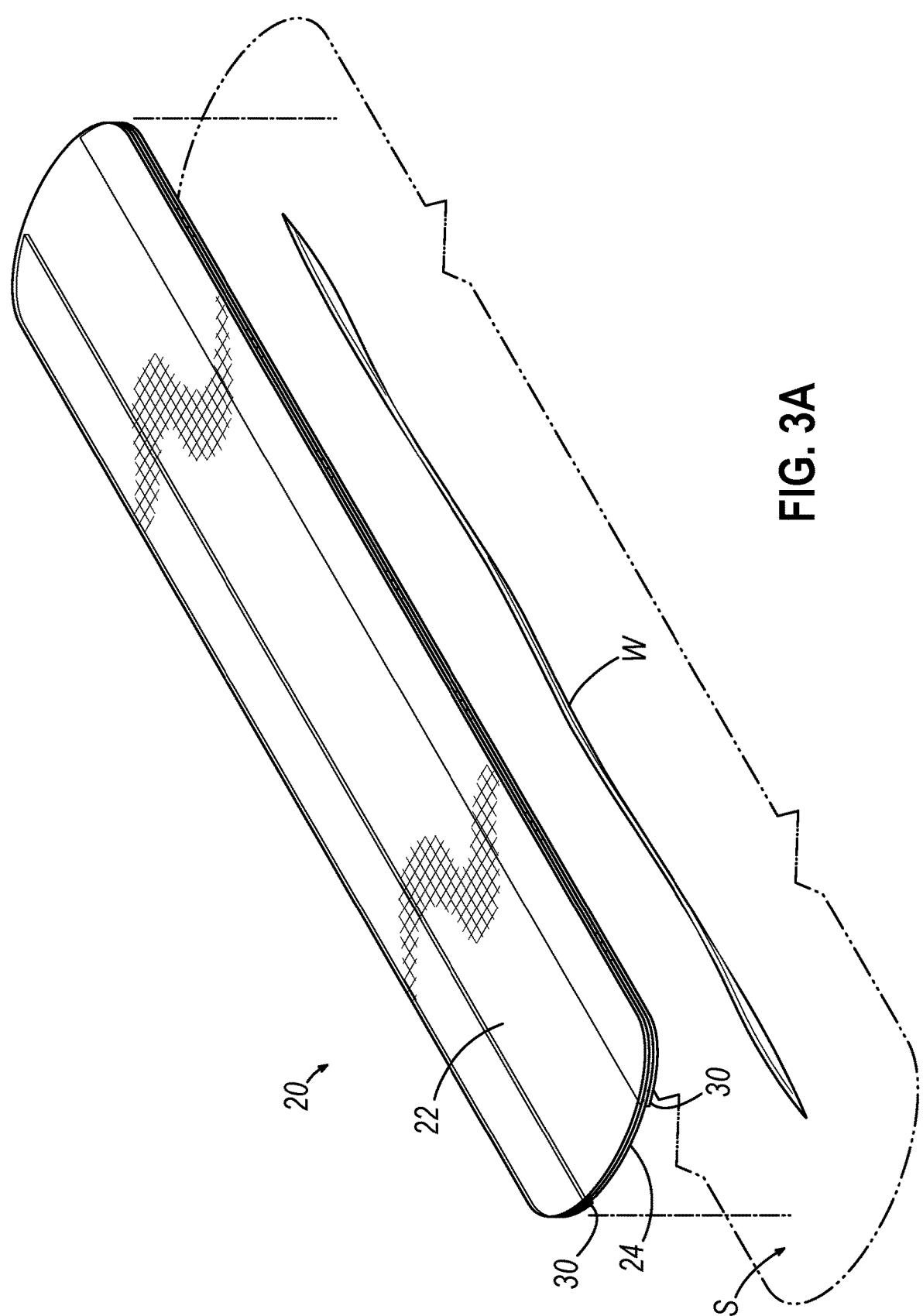
FIG. 3A depicts a perspective view of the wound closure device of FIG. 1 aligned longitudinally with a wound in the skin of a patient, showing a central section of the backing layer having been removed.
Figure 3B:
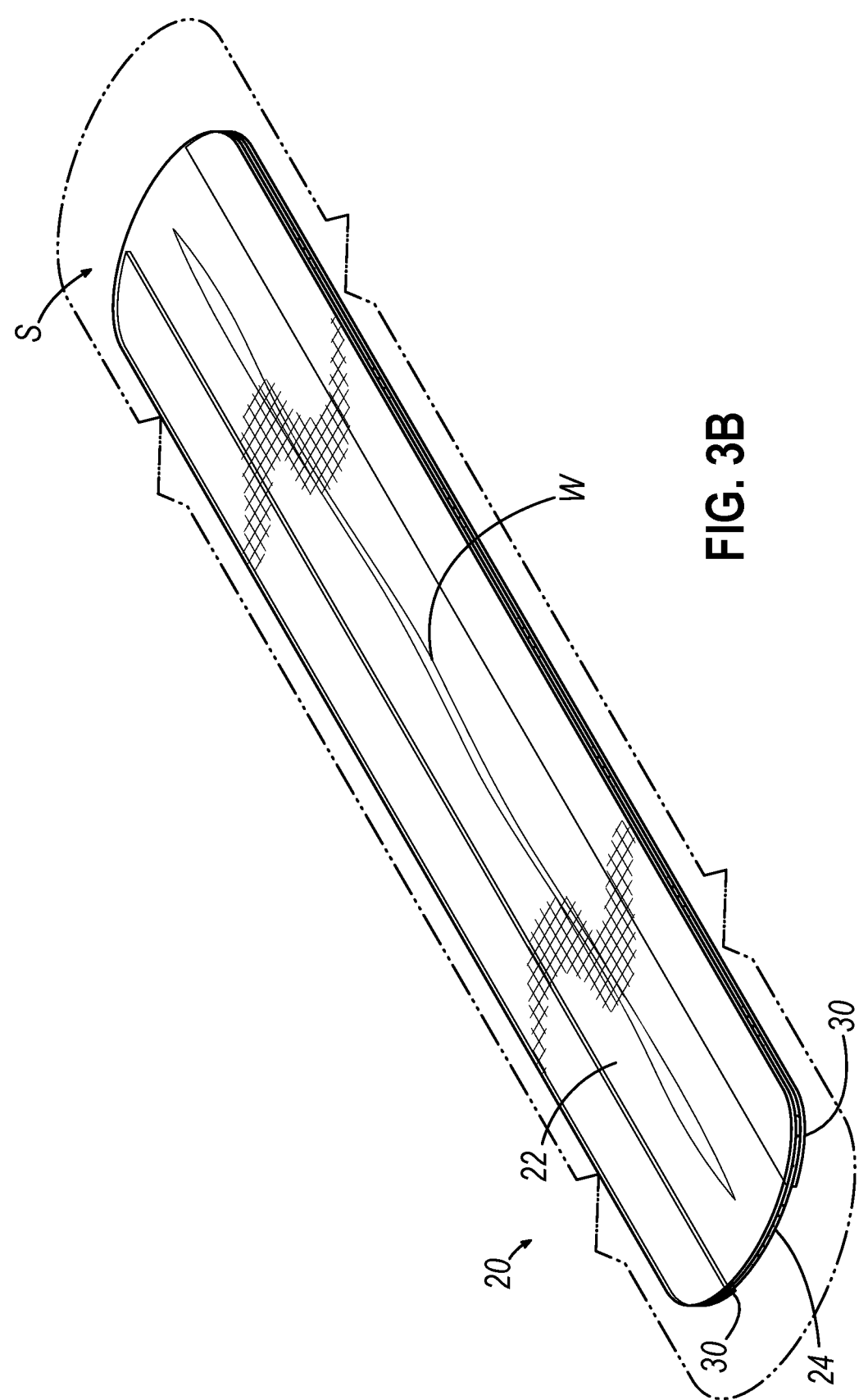
FIG. 3B depicts a perspective view of the wound closure device of FIG. 1 applied to the patient's skin over the wound to approximate the edges of the wound.
Figure 3C:
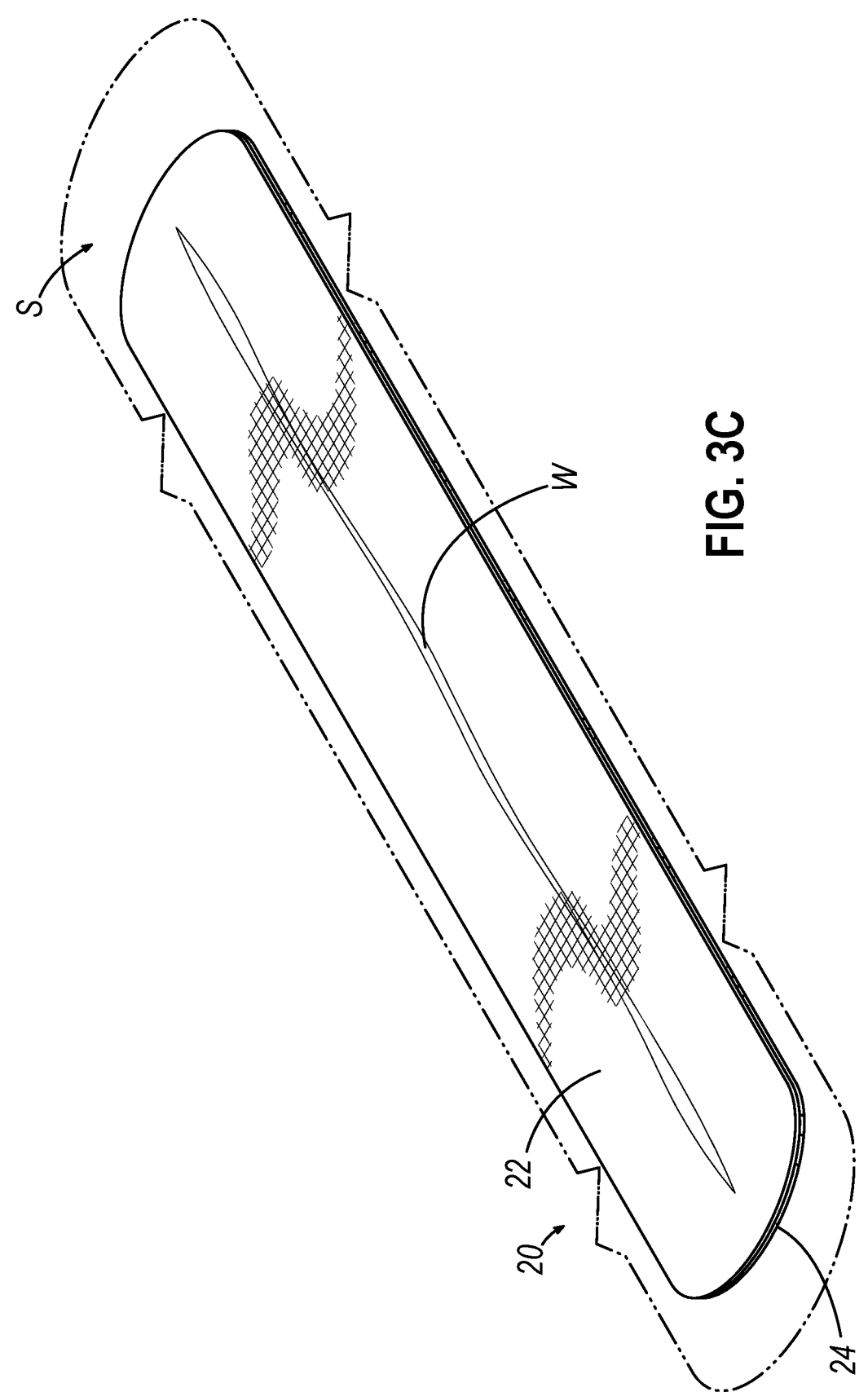
FIG. 3C depicts a perspective view of the wound closure device of FIG. 1 applied to the patient's skin over the wound, showing remaining sections of the backing layer having been removed so the wound closure device is fully adhered to the skin.
Figure 3D:
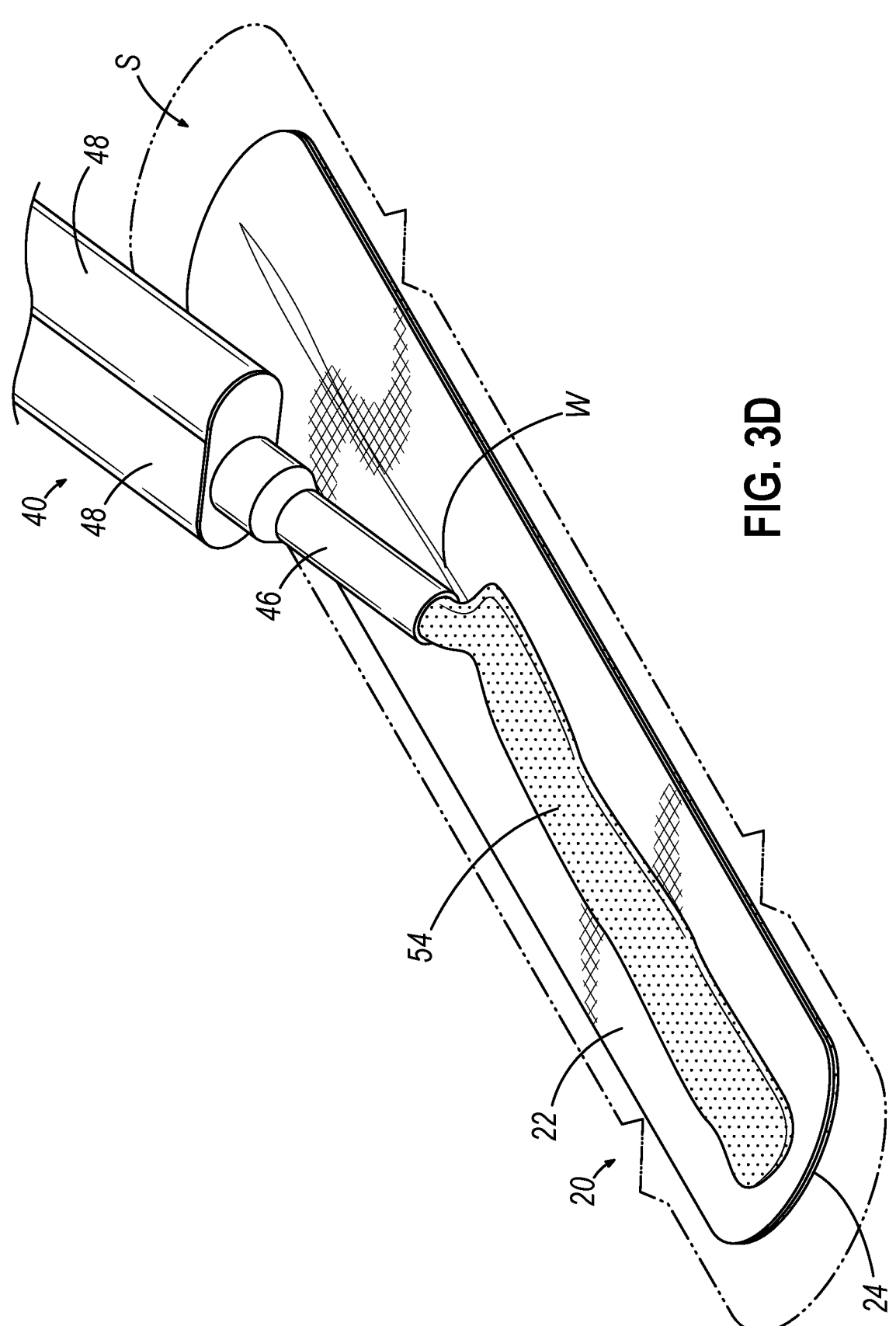
FIG. 3D depicts a perspective view of the wound closure device of FIG. 1 applied to the patient's skin over the wound, showing application of a liquid topical skin adhesive onto the mesh layer with the adhesive applicator.

As shown in FIG. 3A, central backing section (28) is removed from wound closure device (20) to expose a central window of mesh (22) and pressure sensitive adhesive (24), and an imaginary centerline of wound closure device (20) is aligned longitudinally with the edges of wound (W). Wound closure device (20) is then applied to the patient skin (S) over wound (W) and the surgeon applies pressure to the central portion of mesh (22) to force pressure sensitive adhesive (24) to adhere to the skin (S), thus fixing the edges of wound (W) relative to one another. Before this step, the edges of wound (W) may be held in an approximated state by the surgeon. Alternatively, during this step the central portion of wound closure device (20) may be applied in a laterally alternating manner to approximate the edges of wound (W) during application. With either approach, wound closure device (20) is configured to hold the edges of wound (W) in an approximated state following this initial step of application. Once the surgeon is satisfied with the position of wound closure device (20) relative to wound (W), the surgeon may then remove the remaining two side backing sections (30) to adhere the reminder of wound closure device (20) to skin (S).

As shown in FIG. 3D, adhesive applicator (40) is then used to apply a pattern of topical skin adhesive (54) to the upper side of mesh (22) of the applied wound closure device (20). While adhesive applicator (40) is shown applying a linear bead of topical skin adhesive (54) in the present version, it will be appreciated that various other patterns of topical skin adhesive (54) may be applied in other versions, such as a T-shaped pattern or a wave-shaped pattern as disclosed in U.S. Pat. App. Publication No. US2024/0165292A1, entitled "Application of Topical Skin Adhesive to Surgical Mesh," filed on Nov. 22, 2022, the disclosure of which is incorporated by reference herein, in its entirety.

Figure 3E:
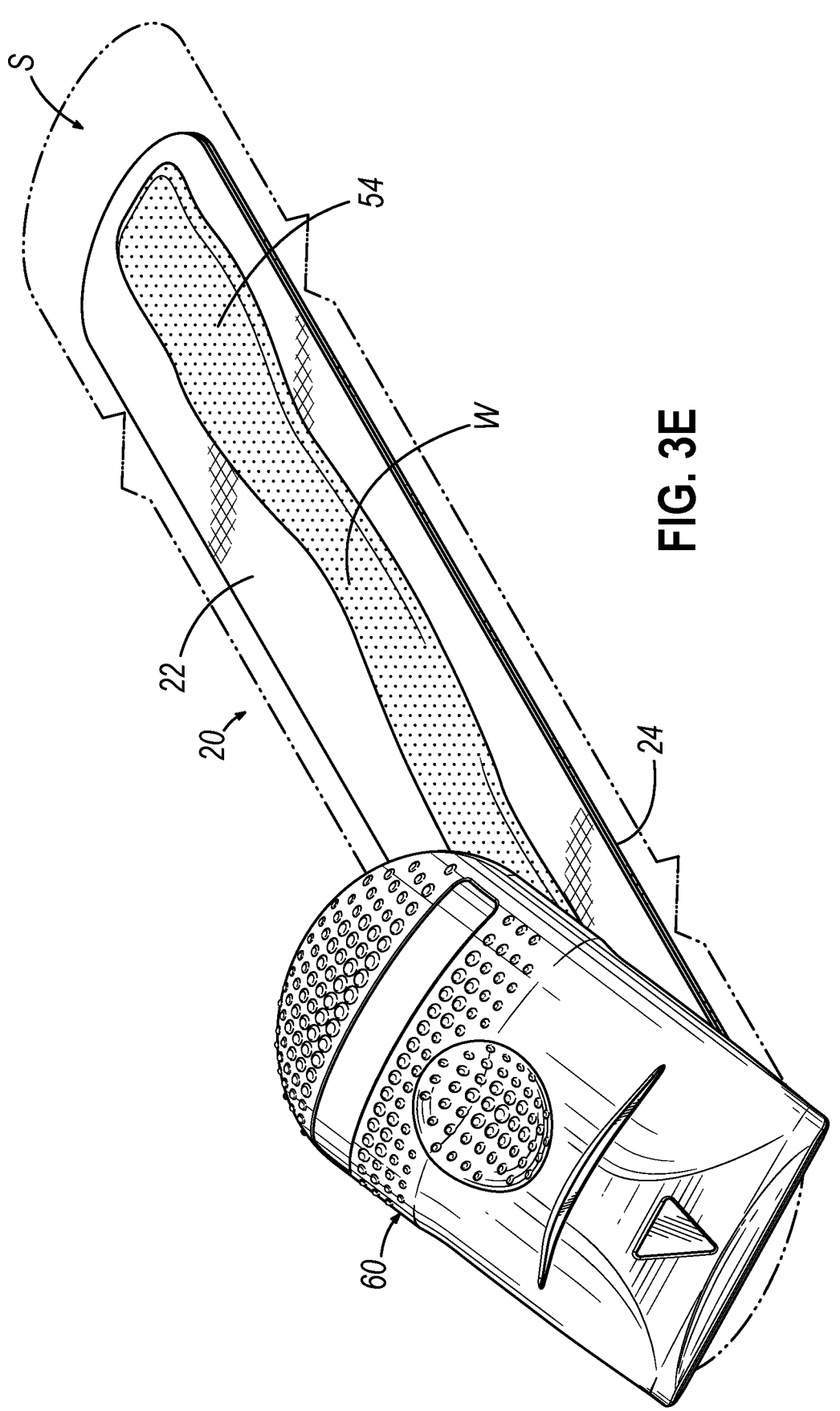
FIG. 3E depicts a perspective view of the wound closure device of FIG. 1 applied to the patient's skin over the wound, showing the adhesive spreader positioned against the patient at the start of an adhesive spreading stroke for spreading the applied topical skin adhesive over and through the wound closure device.
Figure 3F:
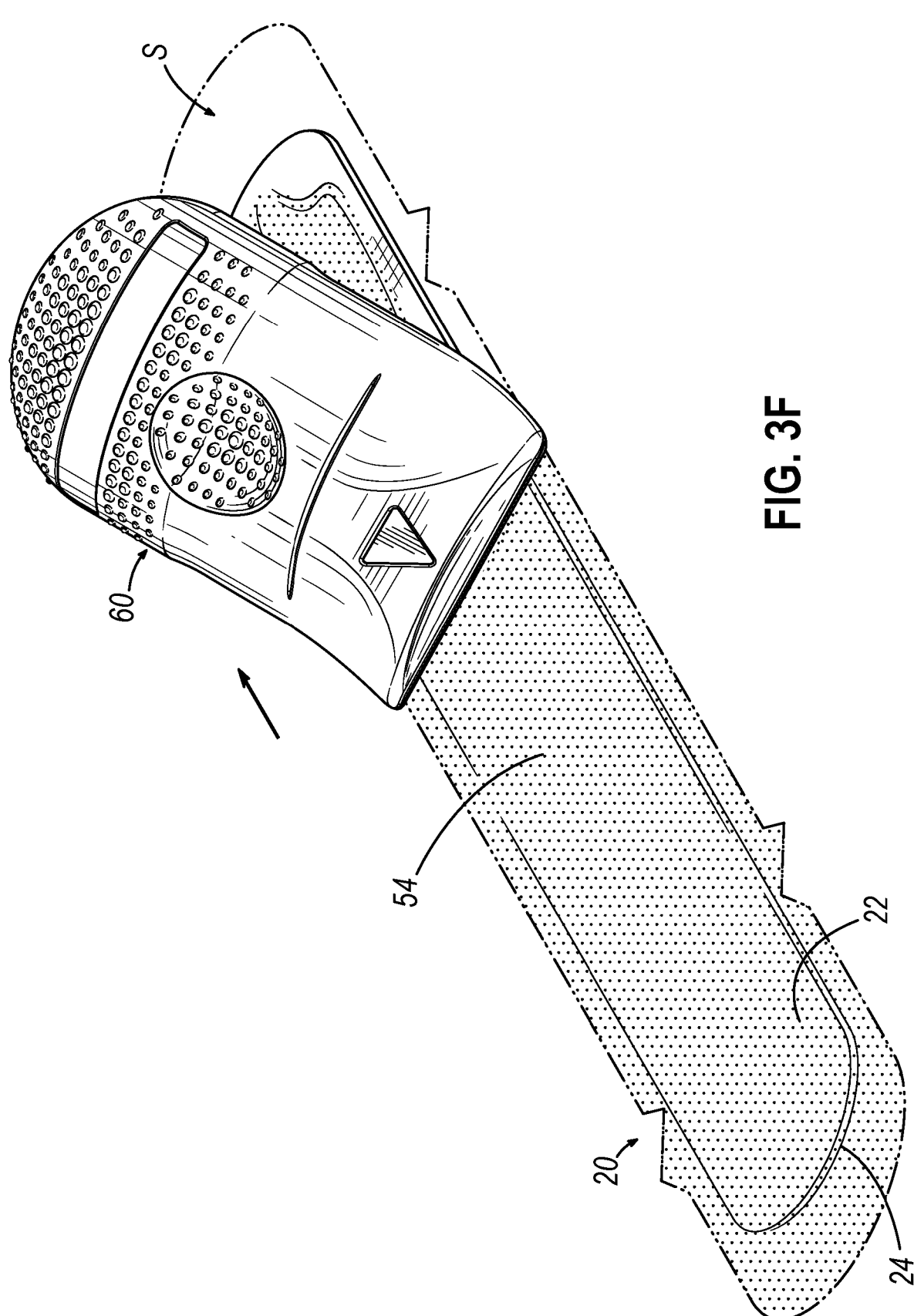
FIG. 3F depicts a perspective view of the wound closure device of FIG. 1 applied to the patient's skin over the wound, showing the adhesive spreader during a subsequent portion of the adhesive spreading stroke.

As shown in FIGS. 3E-3F, adhesive spreader (60) is then used to spread the applied topical skin adhesive (54) uniformly over wound closure device (20) to force the topical skin adhesive (54) through the layers of mesh (22) and pressure sensitive adhesive (24) and directly against wound (W) and the surrounding skin (S). In that regard, the layers of mesh (22) and pressure sensitive adhesive (24) may be at least partially permeable to permit forced passage of topical skin adhesive (54) therethrough. As shown in FIG. 3E, flexural body portion (66) of adhesive spreader (60) may be in a non-deformed state when adhesive spreader (60) is first positioned against wound closure device (20) at the beginning of an adhesive spreading stroke. As adhesive spreader (60) is dragged longitudinally along wound closure device (20), the input force exerted by the user may cause flexural body portion (66) to elastically deform such that distal body portion (64) angularly deflects relative to proximal body portion (62), as shown in FIG. 3F. The degree of deformation of flexural body portion (66) may be directly related to the viscosity of topical skin adhesive (54). In particular, a greater viscosity may require that the user exert a greater input force through proximal body portion (62) to effectively spread topical skin adhesive (54) over and through wound closure device (20), such that the flexural body portion (66) deforms a relatively greater amount. Conversely, a lesser viscosity may require a lesser input force such that the flexural body portion (66) deforms less or not at all.

Optionally, topical skin adhesive (54) may also be spread over adjacent portions of skin (S) not covered by wound closure device (20) to ensure that an entirety of mesh (22) is embedded with topical skin adhesive (54). For instance, and by way of example only, topical skin adhesive (54) may be spread onto at least 1 cm of skin (S) about the entire outer perimeter of the applied wound closure device (20). Once topical skin adhesive (54) has been fully spread over wound closure device (20), any topical skin adhesive (54) on skin (S) beyond the perimeter of device (20) may then be wiped away with sterile gauze, for example. Additionally, in some instances, a quantity of topical skin adhesive (54) may be applied between the edges of wound (W) before wound closure device (20) is applied to the skin (S). The applied topical skin adhesive (54) then cures within and over wound closure device (20) to form a composite microbial barrier over wound (W) that maintains a protective environment that promotes efficient healing. Following healing of wound (W), wound closure device (20) may be removed from the skin (S) manually (e.g., by a surgeon) or it may automatically separate from the skin (S) such that it may be discarded by the patient.

Wound closure system (10) may be further configured and operable in accordance with at least some of the teachings of U.S. Pat. No. 11,712,229, entitled "Systems, Devices and Methods for Dispensing and Curing Silicone Based Topical Skin Adhesives," issued Aug. 1, 2023, the disclosure of which is incorporated by reference herein, in its entirety; U.S. Pat. No. 11,518,604, entitled "Systems, Methods and Devices for Aerosol Spraying of Silicone Based Topical Skin Adhesives for Sealing Wounds," issued Dec. 6, 2022, the disclosure of which is i ncorporated by reference herein, in its entirety; U.S. Pat. No. 11,479,669, entitled "Novel Topical Skin Closure Compositions and Systems," the disclosure of which is incorporated by reference herein, in its entirety; U.S. Pat. No. 12,465,577, entitled "Novel Antimicrobial Topical Skin Closure Compositions and Systems," issued Nov. 11, 2025, the disclosure of which is incorporated by reference herein, in its entirety; U.S. Pat. No. 11,589,867, entitled "Anisotropic Wound Closure Systems," issued Feb. 28, 2023, the disclosure of which is incorporated by reference herein, in its entirety; and/or U.S. patent application Ser. No. 17/667,950, entitled "Gas Sterilizable Syringes Having Apertures Covered By Gas Permeable Barriers For Enabling Ingress and Egress of Sterilization Gases While Preventing Leakage of Flowable Materials," filed on Feb. 9, 2022, published as U.S. Pub. No. 2022/0395643 on Dec. 15, 2022, the disclosure of which is incorporated by reference herein, in its entirety.

II. Illustrative Wound Closure System having Microcannulaic Pathways

As mentioned above, after wound closure device (20) is applied to wound (W) in accordance with the description above, topical adhesive (54) is suitably applied within and over wound closure device (20) to form a composite microbial barrier over wound (W), thereby maintaining a protective environment that promotes effective healing. Such a microbial barrier may effectively seal the wound (W) from the external environment.

In some instances, after wound closure device (20) and topical adhesive (54) are suitably applied over wound (W), exudate and/or other matter may accumulate within wound (W). With wound (W) effectively sealed from the external environment, accumulation of exudate and/or other matter within wound (W) may lead to undesirable consequences, such as infection, inhibiting wound closure and/or other undesirable consequences that would be apparent to one skilled in the art in view of the teachings herein. Therefore, it may be desirable to have a wound closure system capable of removing accumulated exudate and/or other matter after wound closure device and topical adhesive (54) are suitably applied.

Figure 4:
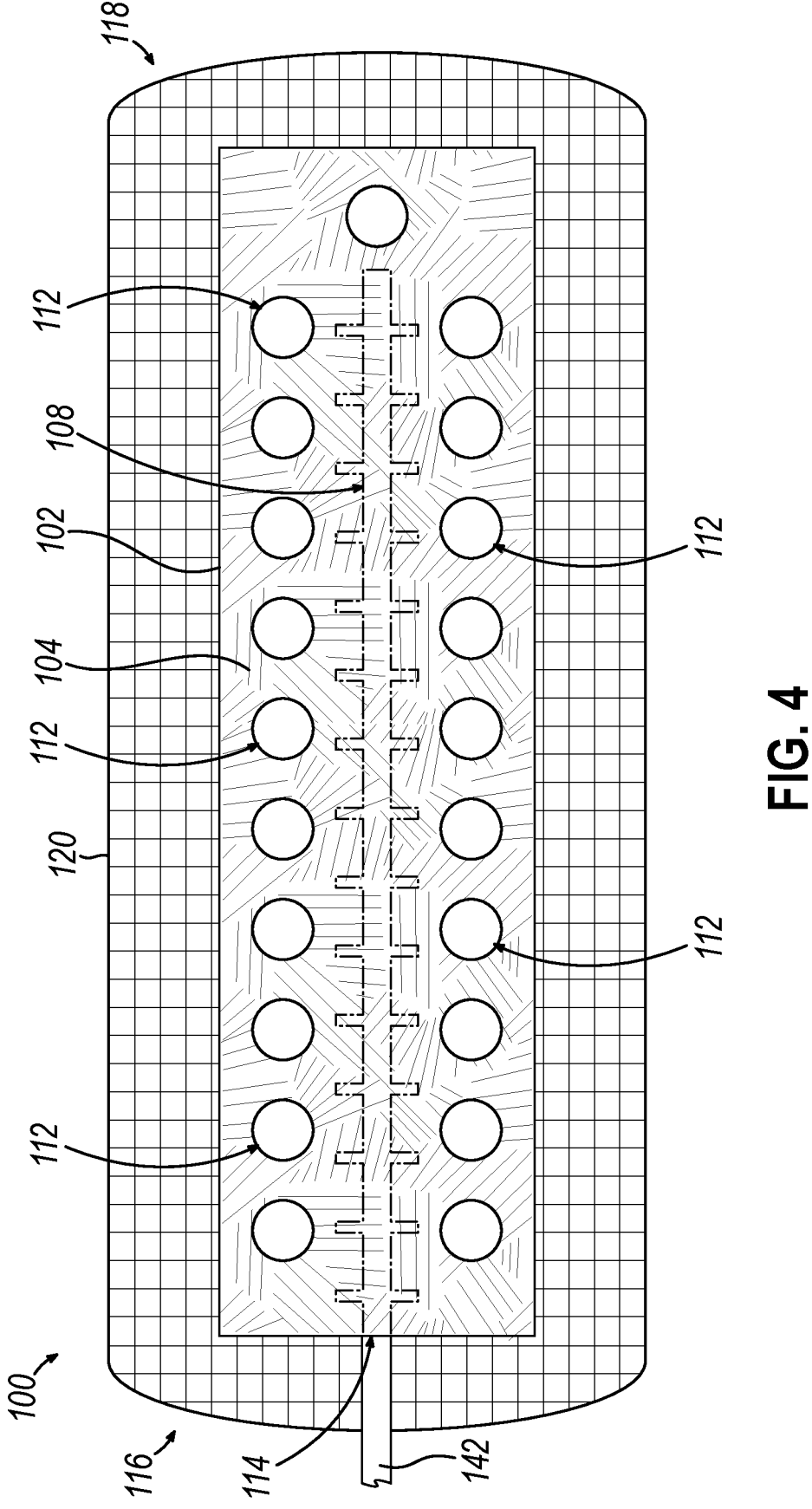
FIG. 4 depicts a top plan view of an alternative wound closure system including a suction distribution member and a wound closure patch.

FIG. 4 shows an illustrative wound closure system (100) that may be utilized in replacement of wound closure system (10) described above. Therefore, wound closure system (100) is configured to close a wound (W) formed in the skin (S) of patient while forming a microbial barrier in conjunction with topical skin adhesive (54). Additionally, as will be described in greater detail below, wound closure system (100) is also configured to provide a suitable amount of suction within wound (W) to remove accumulated exudate and/or other matter after the microbial barrier is formed.

Wound closure system (100) includes a wound closure patch (102) and a suction distribution member (120). As a shown in FIGS. 5A-5B, suction distribution member (120) is configured to be placed on top of skin (S) to thereby cover the wound (W). In the current example, suction distribution member (120) includes an open cell porous sponge that is configured to distribute suction from openings (110) defined on an underside (106) (see FIG. 5C) of wound closure patch (102) into wound (W); while also allowing for exudate and/or other matter to be suctioned out of wound (W) and into a channel (108) defined by wound closure patch (102). Suction distribution member (120) may be formed of any suitable material, or combination of materials, as would be apparent to one skilled in the art in view of the teachings herein.

In some instances, suction distribution member (120) may include a layer of pressure sensitive adhesive and backing, which may be substantially similar to pressure sensitive adhesive (24) and backing (26) described above. Therefore, a surgeon may utilize pressure sensitive adhesive to temporarily attach suction distribution member (120) to skin (S) and wound (W) in substantially the same manner as wound closure device (20) described above. In some instances, suction distribution member (120) may be entirely omitted, such that wound closure patch (102) is placed on top of skin (S) to thereby cover wound (W).

In the current aspect of the disclosure, wound closure patch (102) has a generally rectangular shape and extends longitudinally from a proximal end (116) toward a distal end (118). As best seen in FIGS. 5C-5D and FIGS. 6A-6C, wound closure patch (102) has a top surface (104) and a bottom surface (106) that together define a thickness for wound closure patch (102).

Wound closure patch (102) is suitably dimensioned to define a longitudinally extending channel (108); while bottom surface (106) defines a plurality of openings (110) in fluid communication with channel (108). Openings (110) are arranged along the length of longitudinally extending channel (108). Additionally, wound closure patch (102) is dimensioned to be placed over the length of wound (W) such that channel (108) and openings (110) are adjacent to wound (W). In some instances, wound closure patch (102) may be placed over selected portions of wound (W). Therefore, it should be understood that wound closure patch (102) may have any suitable dimensions as would be apparent to one skilled in the art in view of the teachings herein.

Figure 6A:
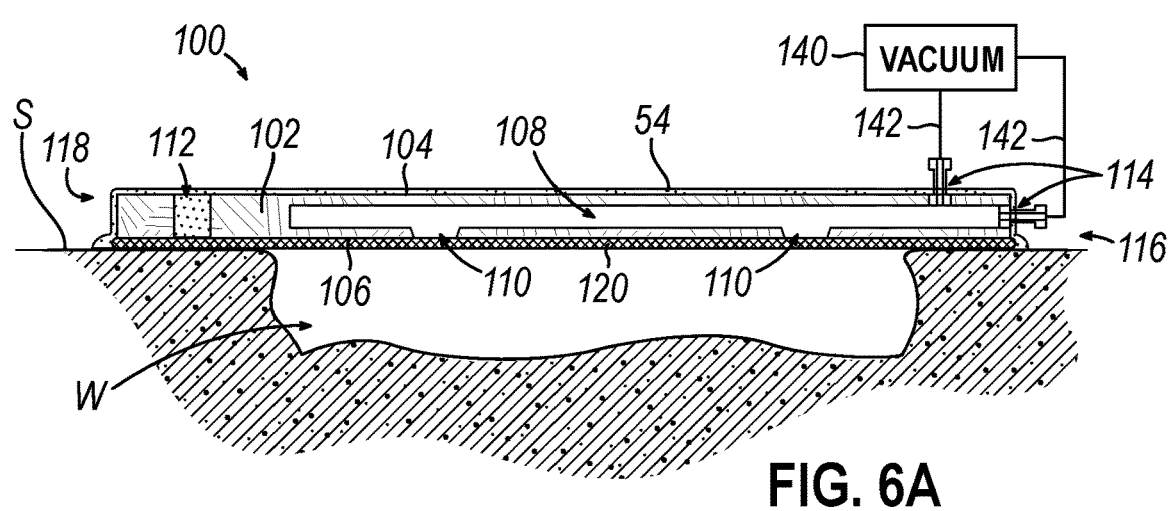
FIG. 6A depicts a cross-sectional view, taken along line 6-6 of FIG. 5E, of the wound closure patch and the suction distribution member of FIG. 4 having a layer of topical skin adhesive covering the wound closure patch and the suction distribution member.
Figure 6B:
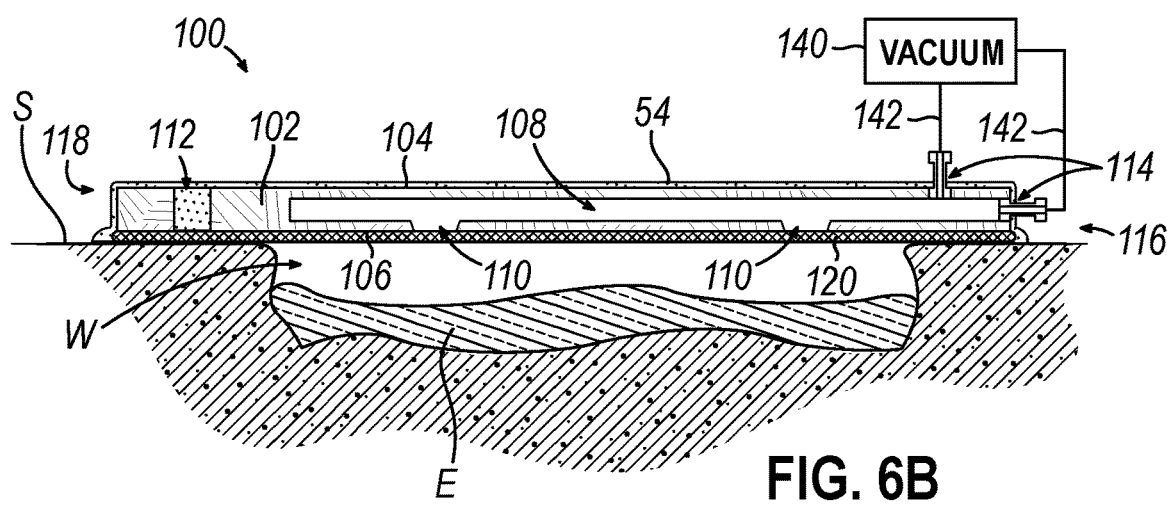
FIG. 6B depicts a cross-sectional view, taken along line 6-6 of FIG. 5E, of the wound closure patch and the suction distribution member of FIG. 4 having a layer of topical skin adhesive as shown in FIG. 6A, with exudate accumulated within the wound.
Figure 6C:
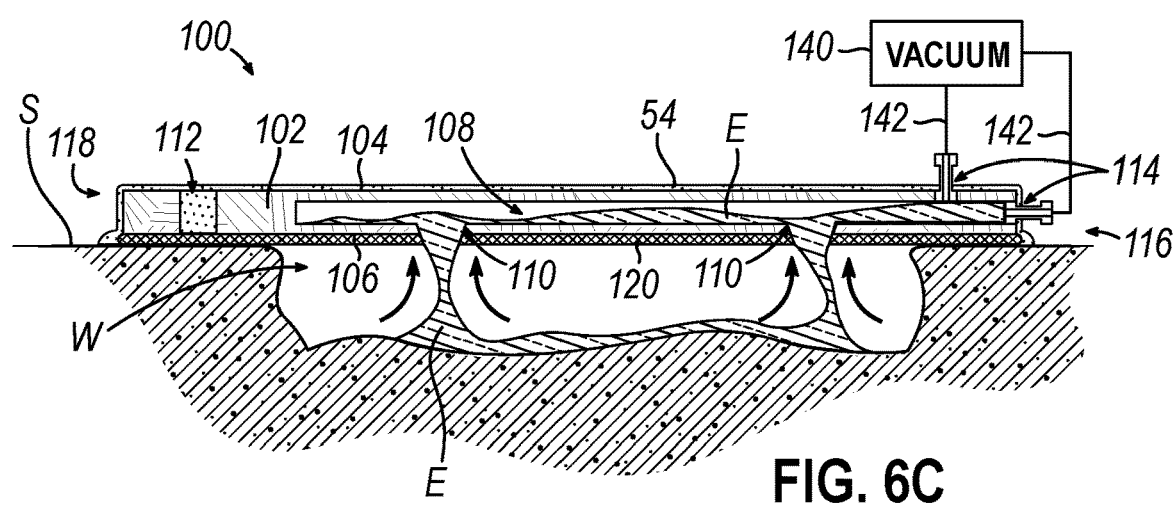
FIG. 6C depicts a cross-sectional view, taken along line 6-6 of FIG. 5E, of the wound closure patch and the suction distribution member of FIG. 4 having a layer of topical skin adhesive as shown in FIG. 6A, with accumulated exudate being suctioned out of the wound via the wound closure patch.
Figure 7:
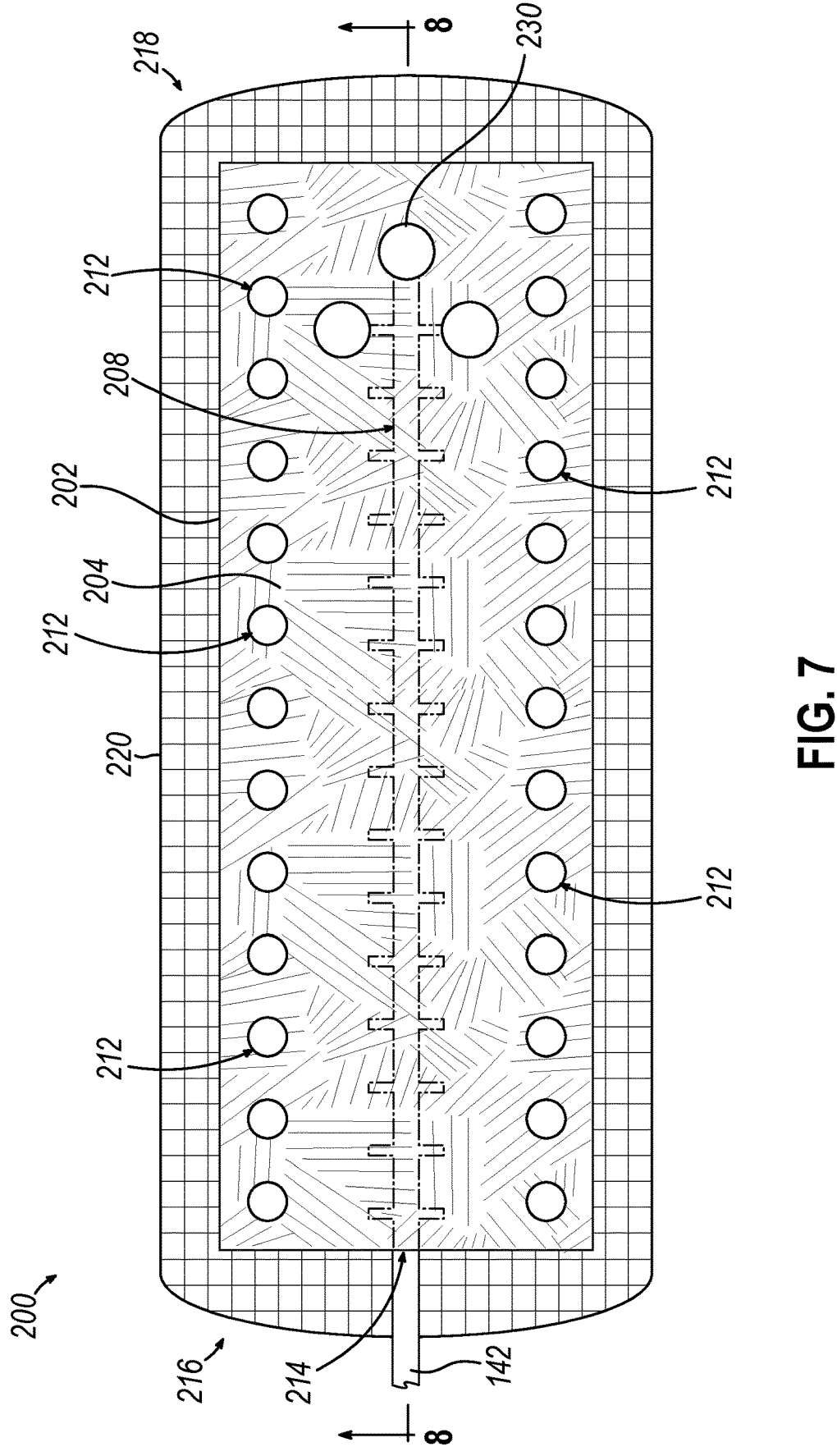
FIG. 7 depicts a top plan view of an alternative wound closure system including a suction distribution member and a wound closure patch.

Patch (102) may be formed of material configured to suitably conform to the contour of skin (S) such that patch (102) may accommodate movement of a patient while remaining operatively engaged with skin (S) and wound (W). Additionally, patch (102) defines a plurality of topical adhesive receiving pores (112). In the current aspect of the disclosure, pores (112) extend from top surface (104) to bottom surface (106). As best shown in FIGS. 6A-6C, pores (112) are dimensioned to receive topical adhesive (54) when applied and spread onto patch (102) in accordance with the description herein. Therefore, when topical adhesive (54) cures, pores (112) may promote topical adhesive (54) further securing patch (102) onto skin (S) of the patient while creating a microbial barrier. In some instances, bottom surface (106) may include a pressure sensitive adhesive to help promote initially securing patch (102) to either suction distribution member (120) or skin (S) of patient directly.

As best shown in FIGS. 6A-6C, proximal end (116) of wound closure patch (102) includes at least one sealed cannula coupling section (114) in fluid communication with a suction source (140) via cannula (142). Cannula coupling sections (114) are also in fluid communication with channel (108) of patch (102). Therefore, openings (110) and channel (108) are in fluid commutation with suction source (140) when cannulas (142) are coupled to both suction source (140) and cannula coupling sections (114) of patch (102).

Suction source (140) is configured to selectively apply suction when activated such that openings (110) apply suitable suction to wound (W) during illustrative use in accordance with the description herein. Therefore, channel (108) is capable of communicating suction transmitted from cannula (142) to openings (110). Additionally, channel (108) is suitably dimensioned to accommodate exudate and/or other matter that is suctioned from wound (W), through openings (110), and into channel (108) such that suctioned matter may be transferred from channel (108) into cannula (142) and further toward suction source (140). Cannula (142) and suction source (140) may include suitable components and dimensions as would be apparent to one skilled in the art in view of the teaching herein.

With patch (102) defining channel (108) and openings (110), it should be understood that patch (102) is formed from a suitable material that is configured to maintain suitable communication between suction source (140) and wound (W) while deployed in accordance with the description herein. Therefore, patch (102) is sufficiently sturdy to inhibit channel (108) from collapsing in response to suction communicated from suction source (140) to openings (110). Additionally, patch (102) is configured to suitably maintain its structural integrity for at least a predetermined amount of time after being deployed to promote wound healing in accordance with the description herein while also providing suction between suction source (140) and wound (W).

Figure 5A:
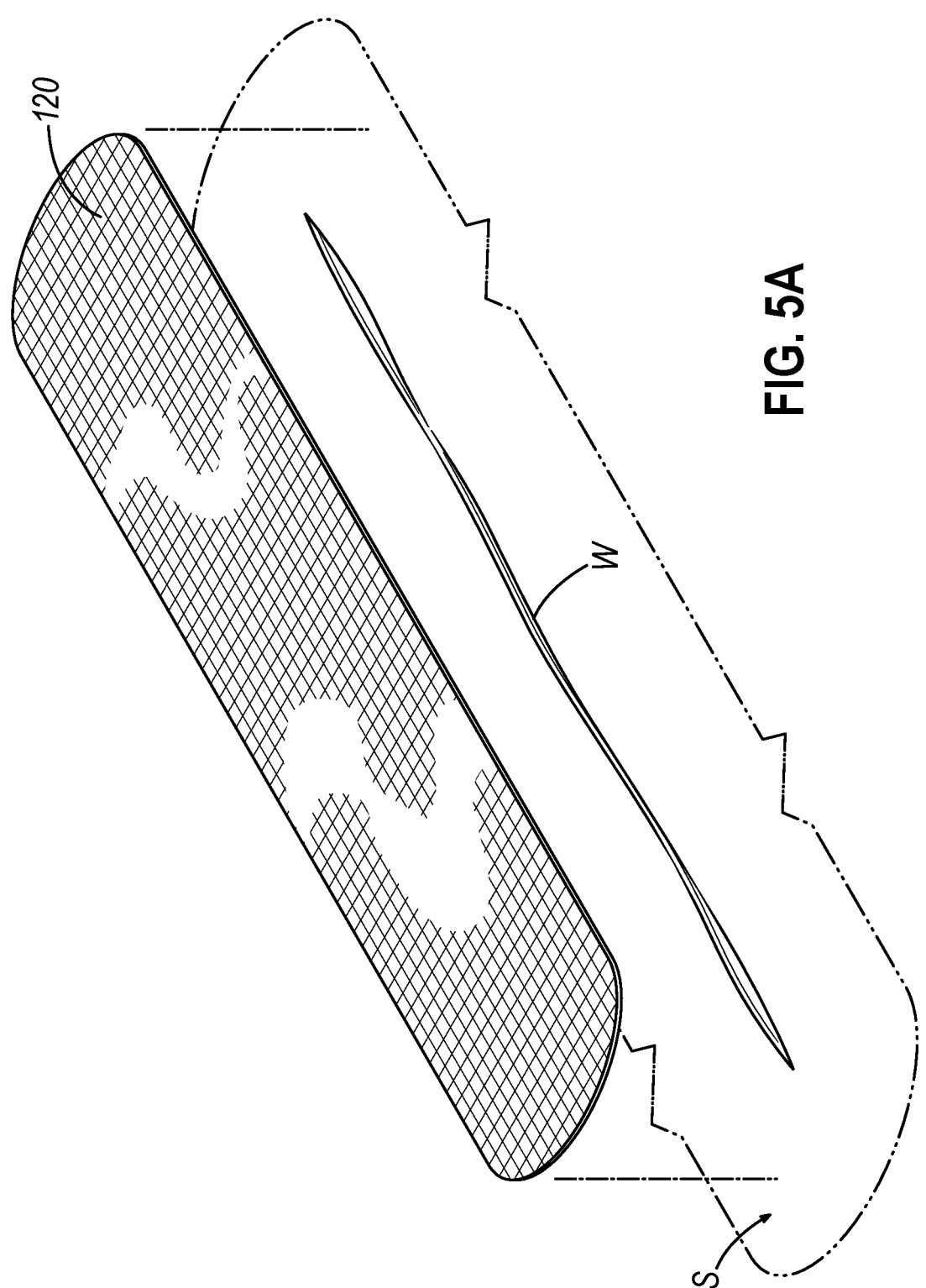
FIG. 5A depicts a perspective view of a suction distribution member of FIG. 4 aligned longitudinally with a wound in the skin of a patient.
Figure 5B:
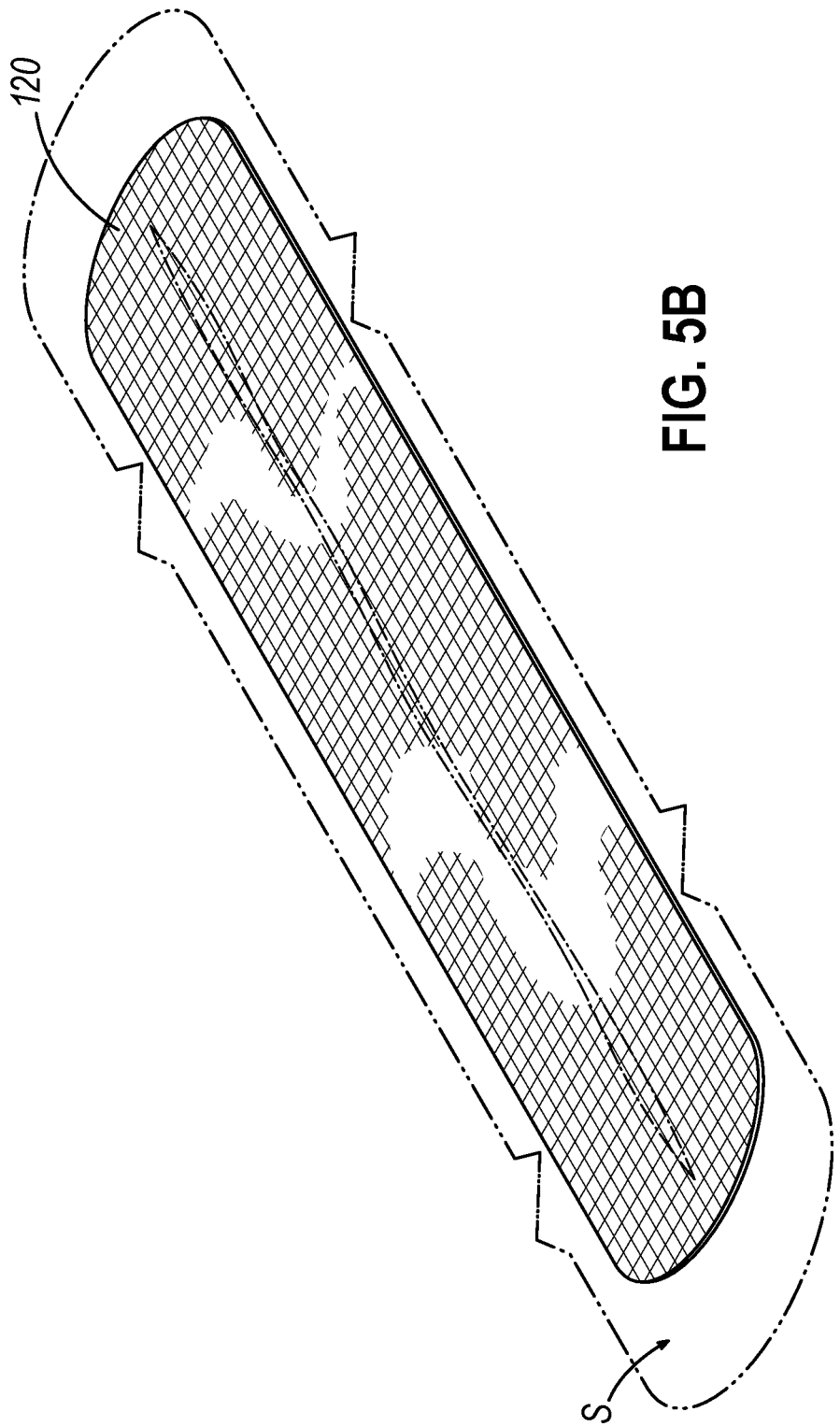
FIG. 5B depicts a perspective view of the suction distribution member of FIG. 4 applied to the patient's skin over the wound to approximate the edges of the wound.

FIGS. 5A-5E show an example of wound closure system (100) being used to close a wound (W) formed in the skin (S) of a patient; while FIGS. 6A-6C show wound closure system (100) being used to remove exudate (E) from the wound (W) of the patient. First, as shown in FIG. 5A, suction distribution member (120) is aligned longitudinally with the edges of wound (W). Next, as shown in FIG. 5B, suction distribution member (120) is then applied to the patient skin (S) over wound (W). As mentioned above, suction distribution member (120) may include a pressure sensitive adhesive, such that the surgeon may apply pressure to suction distribution member (120) to adhere to skin (S).

Figure 5C:
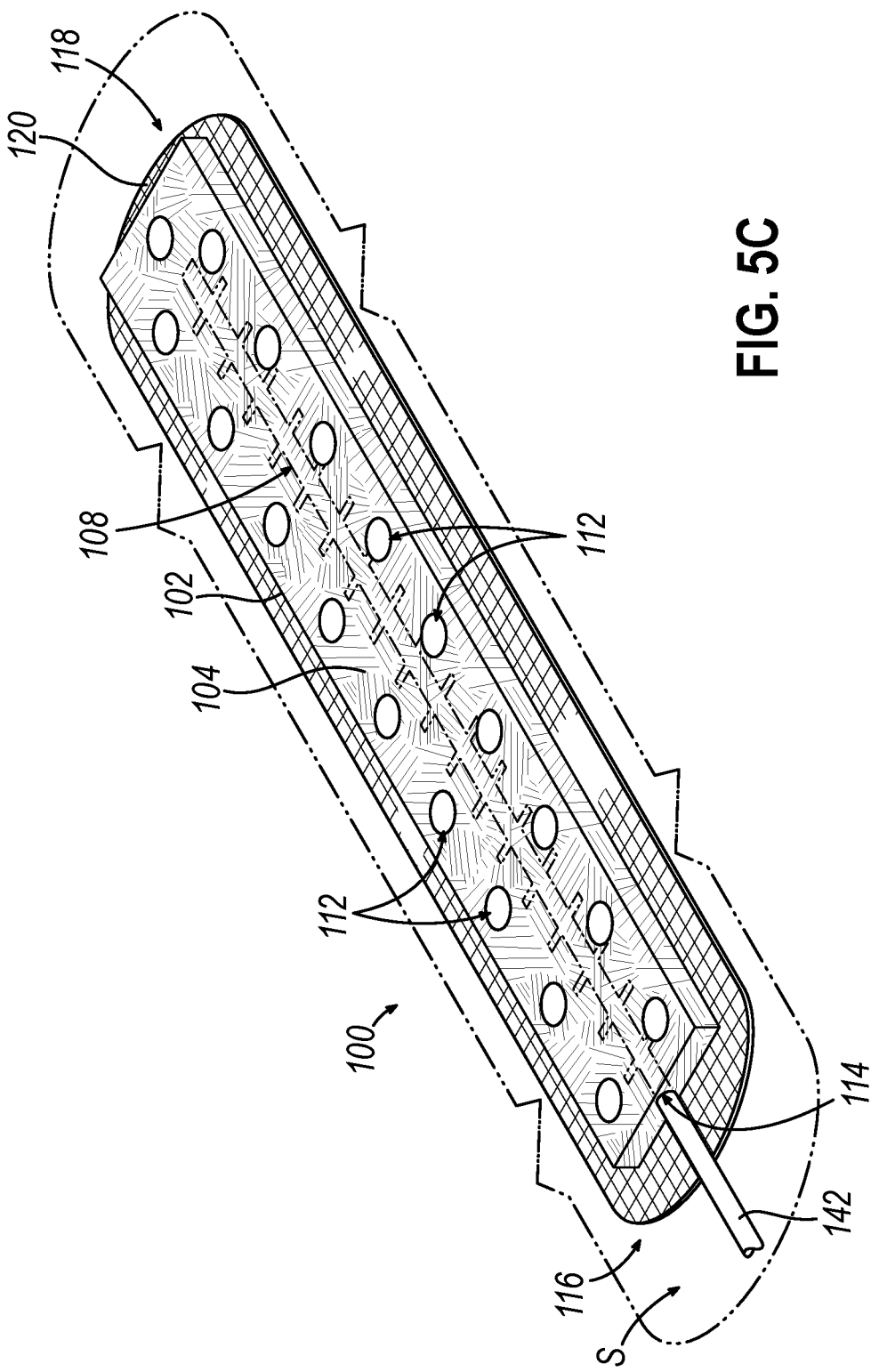
FIG. 5C depicts a perspective view of the wound closure patch of FIG. 4 applied on top of the suction distribution member of FIG. 4, where a longitudinal channel and corresponding array of openings on an underside of the wound closure patch are aligned with the wound in the skin of the patient.
Figure 5D:
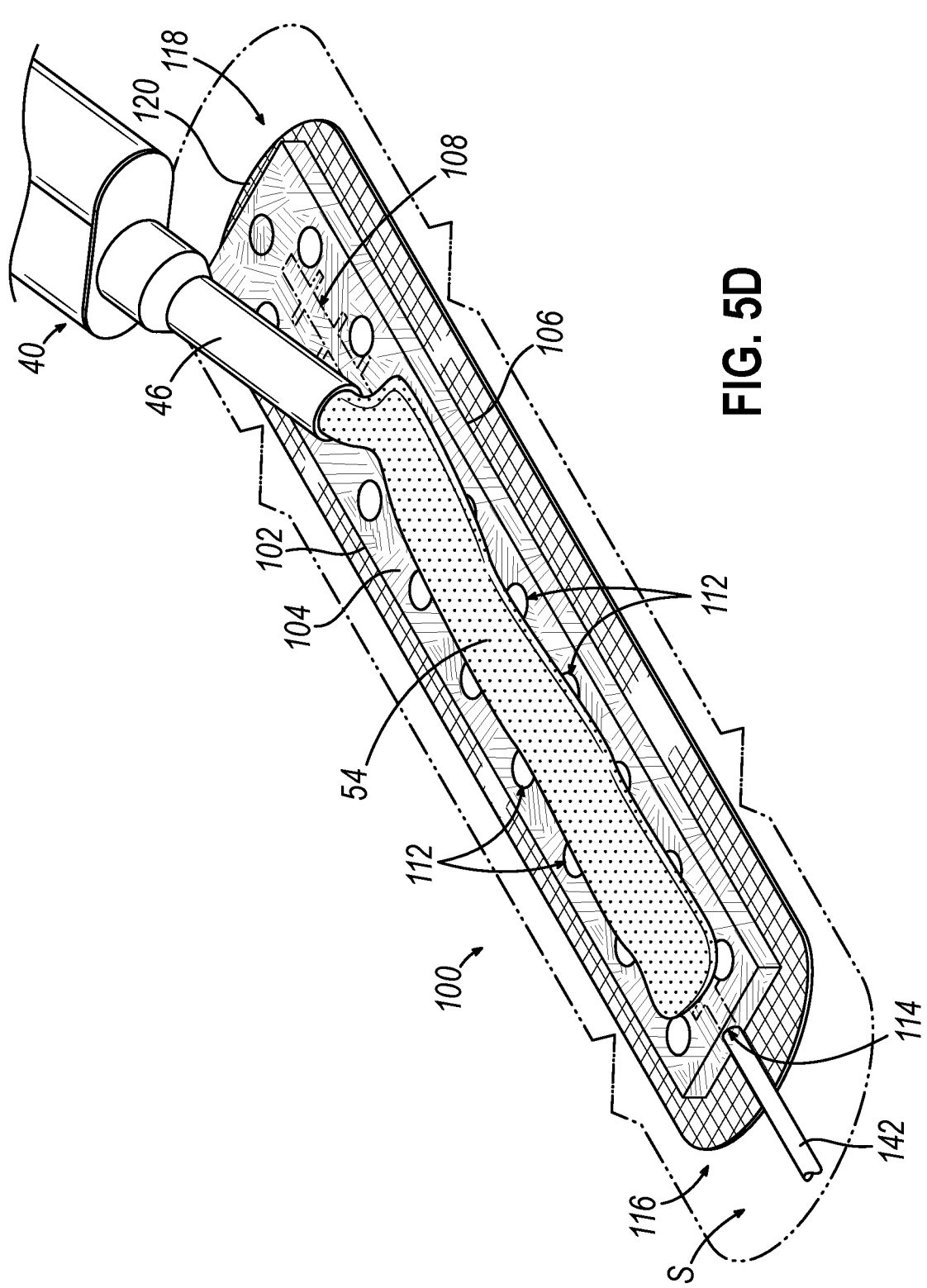
FIG. 5D depicts a perspective view of the wound closure patch and the suction distribution member of FIG. 4, showing application of a liquid topical skin adhesive onto the wound closure patch with the adhesive applicator.

Next, as shown in FIG. 5C, wound closure patch (102) may be applied to the top surface of suction distribution member (120) such that communication channel (108) and openings (110) extend adjacent to wound (W). As mentioned above, in some instances, suction distribution member (120) is not used. Therefore, in some instances, wound closure patch (102) may be applied directly onto skin (S) to thereby cover wound (W). Once wound closure patch (102) is positioned such that channel (108) and openings (110) are suitably adjacent to wound (W), as shown in FIG. 5D, adhesive applicator (40) is then used to apply a pattern of liquid topical skin adhesive (54) on top surface (104) of patch (102).

Figure 5E:
FIG. 5E depicts a perspective view of the wound closure patch and the suction distribution member of FIG. 4, showing spreading of the topical skin adhesive over and within the wound closure patch and the suction distribution member.

As shown in FIG. 5E, adhesive spreader (60) is then used to spread the applied topical adhesive (54) onto of patch (102), portions of suction distribution member (120), skin (S), and cannula (142). It should be understood that patch may be formed of a material resistant to absorbing topical adhesive (54). Therefore, adhesive spreader (60) may push some topical adhesive (54) into pores (112) of patch (102) to further promote securing patch (102) to skin (S) of patient in accordance with the description herein. The applied topical adhesive (54) then cures over patch (102), portions of suction discussion member (120), skin (S), and cannula (142) to form a composite microbial barrier over wound (W) that maintains a protective environment that promotes efficient healing.

As shown between FIG. 6A-6B, after creating a microbial barrier over wound (W), exudate (E) and/or other matter may tend to accumulate within wound (W) such that exudate (E) may not be able to escape wound (W). In such instances, as shown in FIG. 6C, suction source (140) may be selectively activated in order to generate a suitable negative pressure within wound (W). A suitable negative pressure may generate a suction force within wound (W) such that exudate (E) is suctioned away from wound (W), into channel (108) via openings (110), and into cannula (142) toward suction source (140). Allowing the removal of exudate (E) may promote faster healing of wound (W) or other benefits as would be apparent to one skilled in the art in view of the teachings herein. Negative pressure may be induced within wound (W) for any other suitable purposes as would be apparent to one skilled in the art in view of the teachings herein.

Figure 8A:
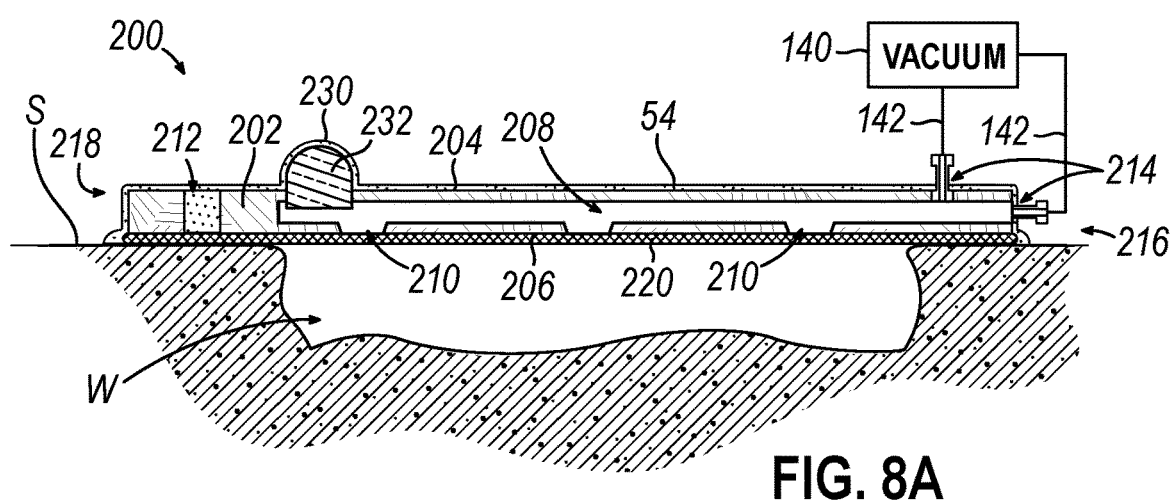
FIG. 8A depicts a cross-sectional view, taken along line 8-8 of FIG. 7, of the wound closure patch and the suction distribution member of FIG. 7 having a layer of topical skin adhesive covering the wound closure patch and the suction distribution member.
Figure 8B:
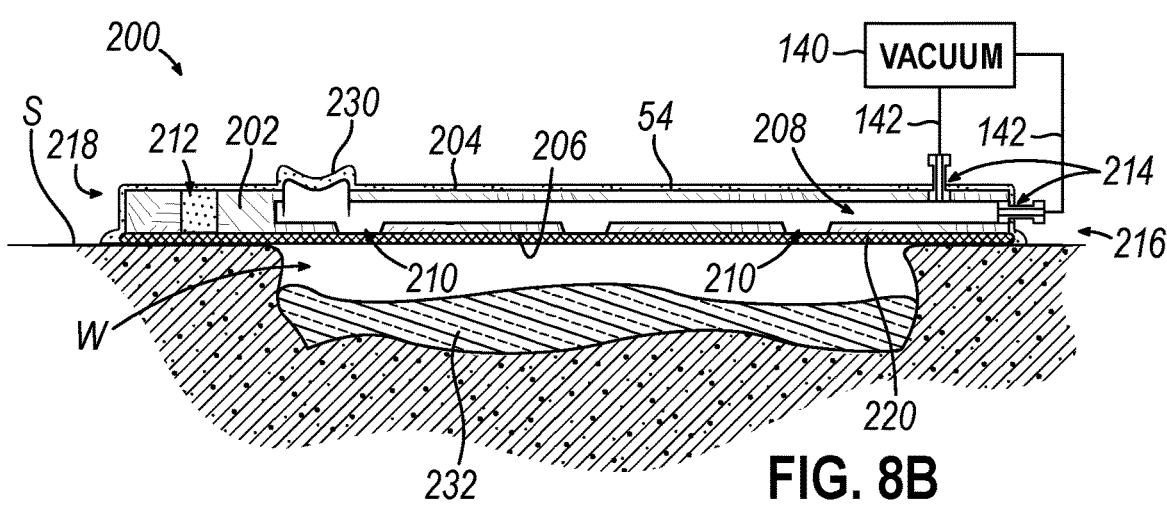
FIG. 8B depicts a cross-sectional view, taken along line 8-8 of FIG. 7, of the wound closure patch and the suction distribution member of FIG. 7 having a layer of topical skin adhesive as shown in FIG. 8A, with a liquid containing blister broken to release liquid within the wound.
Figure 8C:
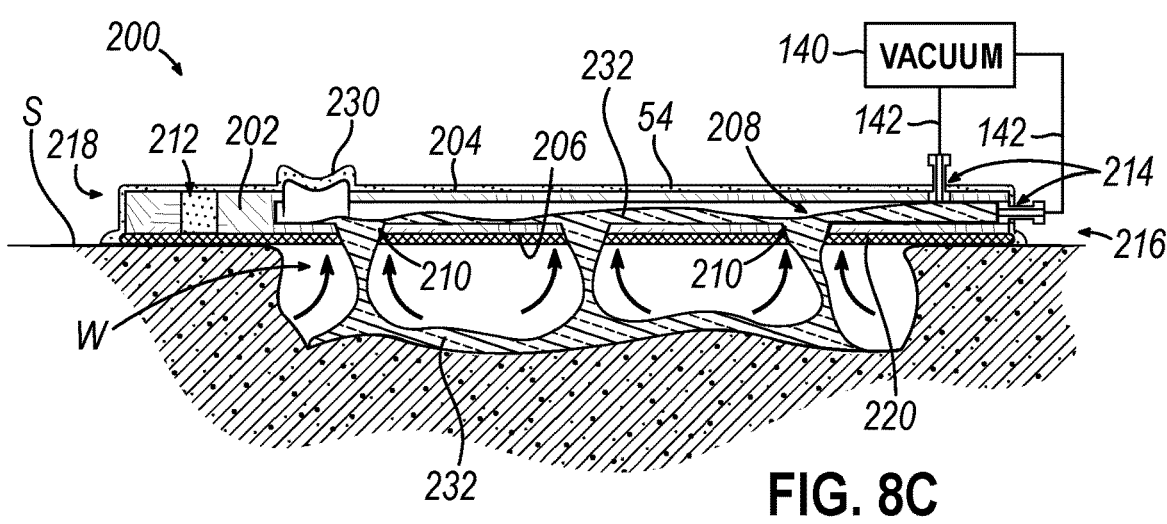
FIG. 8C depicts a cross-sectional view, taken along line 8-8 of FIG. 7, of the wound closure patch and the suction distribution member of FIG. 7 having a layer of topical skin adhesive as shown in FIG. 8A, with accumulated fluid and/or exudate being suctioned out of wound via the wound closure patch.

In some instances, it may be desirable to apply a suitable fluid within wound (W) after creating a microbial barrier over wound (W). For example, in some instances, it may be desirable to insert a therapeutic agent within wound (W) to help further promote efficient healing. FIGS. 8A-8C show another illustrative wound closure system (200) that may be readily incorporated in replacement of wound closure system (100) described above. As will be described in greater detail below, wound closure system (200) is configured to provide suction within wound (W) and also selectively deliver suitable agents into wound (W) after creating a microbial barrier over wound (W).

Wound closure system (200) is substantially similar to wound closure system (100) described above, with differences elaborated below. Therefore, wound closure system (200) includes a suction distribution member (220), a wound closure patch (202) having an upper surface (204), a bottom surface (206), a longitudinal channel (208), an array of openings (210), topical adhesive receiving pores (212), sealed fluid coupling sections (214), a proximal end (216), and a distal end (218); which may be substantially similar to section distribution member (120), wound closure patch (102), upper surface (104), bottom surface (106), longitudinal channel (108), array of opening (110), topical adhesive receiving pores (112), sealed fluid coupling sections (114), proximal end (116), and distal end (118) described above, respectively, with differences elaborated below.

Additionally, patch (202) includes at least one blister pack (230) extending upwardly from upper surface (204). As shown in FIGS. 8A-8C, each blister pack (230) is located adjacent to channel (208). Blister packs (230) are configured to house an agent (232). As best shown in FIG. 8B, if desired, an operator may compress blister pack (230) with a suitable force in order to release agent (232) into channel (208). Agent (232) may then disperse into wound (W) via openings (210). Therefore, after a microbial barrier is formed, a user may compress the portion of cured topical adhesive (54) covering a desired blister pack (230) in order to release agent (232) within wound (W). Any suitable type of agent (232) may be utilized as would be apparent to one skill in the art in view of the teachings herein. For example, agent (232) may include a therapeutic liquid configured to treat wound (W) for an infection. Agent (232) may include a steroid to promote faster healing of wound (W). Agent (232) may include a saline solution. Additionally, blister packs (230) may contain different agents (232) in each pack (230) that may be utilized for different scenarios or in combination with each other to achieve different desired results.

While three blister packs (230) are shown in the current example, any suitable number of blister packs (230) may be utilized as would be apparent to one skilled in the art in view of the teachings herein. Blister packs (230) may include any suitably structures and be formed of any suitable material as would be apparent to one skilled in the art in view of the teaching herein.

Figure 9:
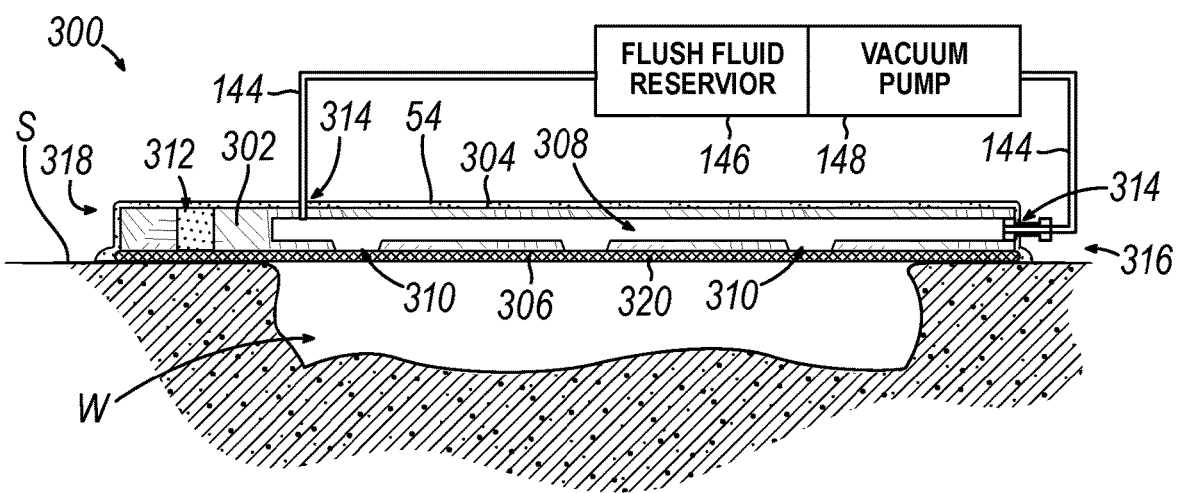
FIG. 9 depicts a central cross-sectional view of another alternative wound closure system.

FIG. 9 shows another illustrative wound closure system (300) that may be readily incorporated in replacement of wound closure system (100) described above. As will be described in greater detail below, wound closure system (300) is configured to selectively deliver suitable fluids into wound (W) and also provide suitable suction after creating a microbial barrier over wound (W).

Wound closure system (300) is substantially similar to wound closure system (100) described above, with differences elaborated below. Therefore, wound closure system (300) includes a suction distribution member (320), a wound closure patch (302) having an upper surface (304), a bottom surface (306), a longitudinal channel (308), an array of openings (310), topical adhesive receiving pores (312), sealed fluid coupling sections (314), a proximal end (316), and a distal end (318); which may be substantially similar to section distribution member (120), wound closure patch (102), upper surface (104), bottom surface (106), longitudinal channel (108), array of opening (110), topical adhesive receiving pores (112), sealed fluid coupling sections (114), proximal end (116), and distal end (118) described above, respectively, with differences elaborated below.

Rather than utilizing blister packs (230) in order to disperse a desired agent into wound (W), wound closure system (300) includes a fluid reservoir (146) in communication with a suction/pump device (148). Fluid reservoir (146) is in fluid communication with channel (308) via cannula (144). Suction/pump device (148) is capable of providing suction within wound (W) or pumping fluid from fluid reservoir (146) into channel (308) and through openings (310). Therefore suction/pump device (148) may be utilized to remove exudate from wound (W) and/or pump a suitable fluid from fluid reservoir (146) into wound (W) via channel (308) and openings (310). While in the current example, a single fluid reservoir (146) is used, any suitable number of fluid reservoirs (146) may be utilized as would be apparent to one skilled in the art in view of the teachings herein. Fluid reservoir (146) may contain any suitable fluid as would be apparent to one skilled in the art in view of the teachings herein. For example, a therapeutic agent, steroid, saline, etc. may be contained within fluid reservoir (146).

Suction/pump deice (148) may include any suitable components as would be apparent to one skilled in the art in view of the teachings herein.

Figure 10:
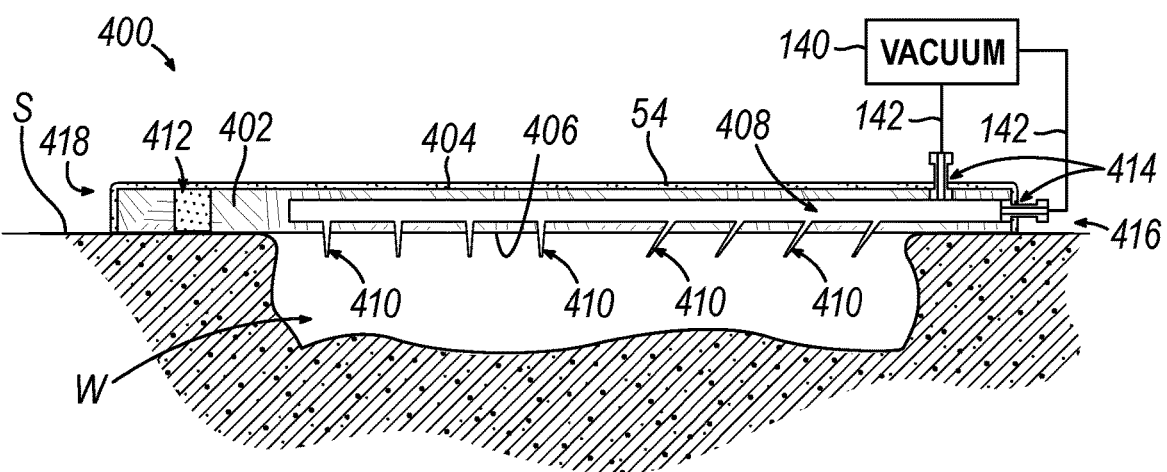
FIG. 10 depicts a central cross-sectional view of another alternative wound closure system.

In some instances, it may be desirable to more accurately control the direction in which suction is imparted into wound (W). Additionally, it may be desirable to more accurately control the direction in which fluids are introduced into wound (W). FIG. 10 shows another illustrative wound closure system (400) that may be readily incorporated in replacement of wound closure system (100) described above. As will be described in greater detail below, wound closure system (400) is configured to apply suction within wound (W) at predetermined directions after creating a microbial barrier over wound (W).

Wound closure system (400) is substantially similar to wound closure system (100) described above, with differences elaborated below. Therefore, wound closure system (400) a wound closure patch (402) having an upper surface (404), a bottom surface (406), a longitudinal channel (408), topical adhesive receiving pores (412), sealed fluid coupling sections (414), a proximal end (416), and a distal end (418); which may be substantially similar to wound closure patch (102), upper surface (104), bottom surface (106), longitudinal channel (108), topical adhesive receiving pores (112), sealed fluid coupling sections (114), proximal end (116), and distal end (118) described above, respectively, with differences elaborated below.

Rather than having a plurality of openings (110) providing fluid communication between channel (408) and wound (W), wound closure patch (402) includes a plurality of atraumatic nozzles (410) extending downward from bottom surface (406) into wound (W). Atraumatic nozzles (410) are positioned along channel (408) such that when patch (402) is applied to skin (S) in order to cover wound (W), atraumatic nozzles (410) may extend within wound (W). Atraumatic nozzles (410) may allow suction to provided deeper within wound (W). Additionally, atraumatic nozzles (410) may extend from bottom surface (406) at a desirable angle, thereby providing control of the direction which suction is applied.

Atraumatic nozzles (410) are sufficiently small enough to prevent inadvertently inhibiting wound (W) from suitably healing. Additionally atraumatic nozzles (410) are formed of a suitable material such that if nozzles (410) abut against skin (S) rather than suitably extend within wound (W) after patch (402) is secured to patient in accordance with the teaching herein, nozzles (410) may suitably deform without damaging skin (S) of the patient. Additionally, atraumatic nozzles (410) may be suitably resilient such that nozzles (410) return to their intended shape after the deformation force (e.g., contact with skin (S)) is no longer present. Therefore, atraumatic nozzles (410) may provide a greater degree of access within wound (W) without inadvertently causing damage to skin (S) or indivertibly inhibiting efficient healing of wound (W).

In the current example, patch (402) is shown without use of a suction distribution member.

Figure 11:
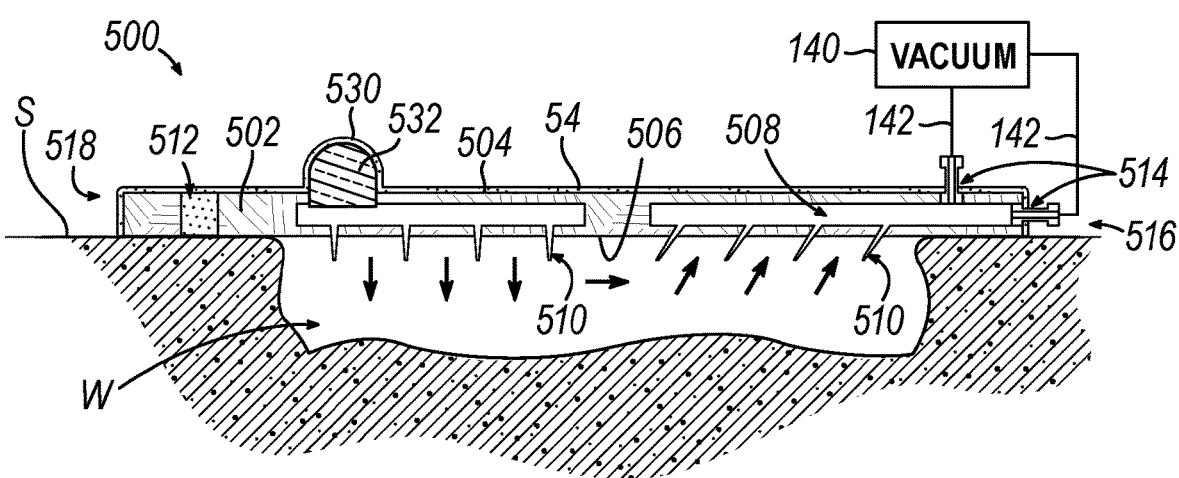
FIG. 11 depicts a central cross-sectional view of another alternative wound closure system.

FIG. 11 shows another illustrative wound closure system (500) that may be readily incorporated in replacement of wound closure system (200) described above. Wound closure system (500) is substantially similar to wound closure system (200) described above, with difference elaborated below. Therefore, wound closure system (500) includes a wound closure patch (502) having an upper surface (504), a bottom surface (506), a longitudinal channel (508), topical adhesive receiving pores (512), sealed fluid coupling sections (514), a proximal end (516), a distal end (518), and blister packs (530) filled with an agent (532); which may be substantially similar to wound closure patch (202), upper surface (204), bottom surface (206), longitudinal channel (208), topical adhesive receiving pores (212), sealed fluid coupling sections (214), proximal end (216), distal end (218), and blister packs (230) filled with agent (232) described above, respectively, with differences elaborated below.

In particular, instead of defining opening (210), wound closure system (500) includes a plurality of atraumatic nozzles (510) that are substantially similar to atraumatic nozzles (410) described above. Therefore, agents (532) may travel into channel (408) and into wound (W) via atraumatic nozzles (410) when blister packs (530) are ruptured in accordance with the description herein. Additionally, suction may be applied via nozzles (510) in similar fashion to nozzles (410) described above. Similar to patch (402) described above, patch (502) is also shown without use of a suction distribution member.

Figure 12:
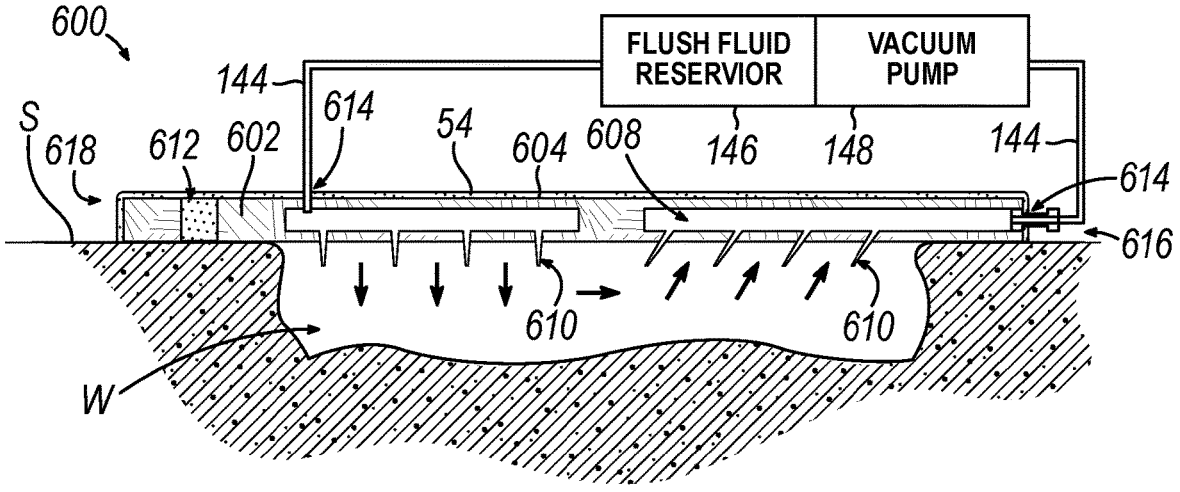
FIG. 12 depicts a central cross-sectional view of another alternative wound closure system.

FIG. 12 shows another illustrative wound closure system (600) that may be readily incorporated in replacement of wound closure system (300) described above. Wound closure system (600) is substantially similar to wound closure system (300) described above, with difference elaborated below. Therefore, wound closure system (600) includes a wound closure patch (602) having an upper surface (604), a bottom surface (606), a longitudinal channel (608), topical adhesive receiving pores (612), sealed fluid coupling sections (614), a proximal end (616), and a distal end (618); which may be substantially similar to wound closure patch (302), upper surface (304), bottom surface (306), longitudinal channel (308), topical adhesive receiving pores (312), sealed fluid coupling sections (314), proximal end (316), and distal end (318), described above, respectively, with differences elaborated below. Therefore, patch (602) is operable to work in conjunction with fluid reservoir (146) and suction/pump device (148) in similar fashion as patch (302) described above.

Instead of defining openings (310), wound closure system (600) includes a plurality of atraumatic nozzles (610) that are substantially similar to atraumatic nozzles (410) described above. Therefore, fluids pumped from fluid reservoir (146) may travel into channel (408) and into wound (W) via atraumatic nozzles (610) when section/pump device (148) is activated in accordance with the description herein. Additionally, suction/pump device (148) may provide suction to wound (W) via nozzles (610) in order to achieve a controlled suction in accordance with the description herein. Similar to patch (402) described above, patch (602) is also shown without use of a suction distribution member.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a cannula configured to establish fluid communication with a suction source; and (b) a wound closure patch dimensioned to cover a wound in skin, wherein the wound closure patch is configured to receive a topical adhesive to thereby adhere to the skin and form a microbial barrier over the wound, wherein the wound closure patch defines a channel, wherein the wound closure patch comprises: (i) a top surface, (ii) a bottom surface defining at least one opening in fluid communication with the channel, wherein the channel is interposed between the top surface and the bottom surface, and (iii) a fluid coupling section in fluid communication with the channel, wherein the fluid coupling section is configured to couple with the cannula to thereby establish fluid communication between the cannula, the channel, and the at least one opening defined by the bottom surface.

Example 2

The apparatus of any one or more of the preceding Examples, wherein the fluid coupling section further comprises a sealed fluid coupling section.

Example 3

The apparatus of any one or more of the preceding Examples, wherein the wound closure patch further defines at least one topical adhesive receiving pore.

Example 4

The apparatus of any one or more of the preceding Examples, wherein the at least one topical adhesive reciting pore extends from the top surface to the bottom surface.

Example 5

The apparatus of any one or more of the preceding Examples, wherein the wound closure patch extends from a proximal end toward a distal end.

Example 6

The apparatus of any one or more of the preceding Examples, wherein the fluid coupling section is located at the proximal end of the wound closure patch.

Example 7

The apparatus of any one or more of the preceding Examples, wherein the channel extends longitudinally from the proximal end toward the distal end.

Example 8

The apparatus of any one or more of the preceding Examples, wherein the top surface comprises a blister pack filled with an agent.

Example 9

The apparatus of any one or more of the preceding Examples, wherein the blister pack is configured to rupture to thereby distribute the agent into the channel.

Example 10

The apparatus of any one or more of the preceding Examples, wherein the agent comprises a therapeutic fluid.

Example 11

The apparatus of any one or more of the preceding Examples, wherein the wound closure patch further comprises at least one atraumatic nozzle in fluid communication with a respective opening of the at least one opening.

Example 12

The apparatus of any one or more of the preceding Examples, wherein the at least one atraumatic nozzle extends downward from the bottom surface of the wound closure patch.

Example 13

The apparatus of any one or more of the preceding Examples, further comprising a second cannula, wherein the wound closure patch comprises a second fluid coupling section in fluid communication with the channel and the second cannula.

Example 14

The apparatus of any one or more of the preceding Examples, wherein the second cannula is configured to establish fluid communication with a fluid reservoir.

Example 15

The apparatus of any one or more of the preceding Examples, further comprising a suctions distribution member configured to abut against the bottom surface of the wound closure patch such that the suction distribution member is interposed between the skin and the wound closure patch.

Example 16

An apparatus, comprising: (a) a cannula configured to establish fluid communication with a suction source; and (b) a wound closure patch dimensioned to cover a wound in skin, wherein the wound closure patch is configured to receive a topical adhesive to thereby adhere to the skin and form a microbial barrier over the wound, wherein the wound closure patch comprises a bottom surface defining a plurality of openings, wherein the wound closure patch defines a longitudinally extending channel in fluid communication with the cannula such that the cannula is configured to induce suction through the plurality of openings via the longitudinally extending channel.

Example 17

The apparatus of any one or more of the preceding Examples, wherein the apparatus further comprises a suction distribution member configured to attach to the bottom surface of the wound closure patch.

Example 18

The apparatus of any one or more of the preceding Examples, wherein the wound closure patch further comprises a plurality of atraumatic nozzles in fluid communication with a respective opening of the plurality of openings.

Example 19

An apparatus, comprising: (a) a wound closure patch dimensioned to cover a wound in skin, wherein the wound closure patch is configured to receive a topical adhesive to thereby adhere to the skin and form a microbial barrier over the wound, wherein the wound closure patch comprises a bottom surface defining a plurality of openings, wherein the wound closure patch defines a longitudinally extending channel in fluid communication with the plurality of openings; and (b) a suction distribution member configured to attach to the bottom surface of the wound closure patch.

Example 20

The apparatus of any one or more of the preceding Examples, wherein the suction distribution member comprises an open cell sponge material.

IV. Miscellaneous

It is understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/427,132, entitled "Device for Spreading Topical Skin Adhesive," filed Nov. 22, 2022, now expired, the disclosure of which is incorporated by reference herein, in its entirety; U.S. Pat. App. No. 17/991,992, entitled "Application of Topical Skin Adhesive to Surgical Mesh," filed Nov. 22, 2022, published as U.S. Pat. Pub. No. 2024/0165292 on May 23, 2024, the disclosure of which is incorporated by reference herein, in its entirety; and/or U.S. patent application Ser. No. 17/991,945, entitled "Surgical Mesh Securing Device for Wound Closure System," filed Nov. 22, 2022, published as U.S. Pat. Pub. No. 2024/0164777 on May 23, 2024, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) a cannula configured to establish fluid communication with a suction source; and (b) a wound closure patch dimensioned to cover a wound in skin, wherein the wound closure patch is configured to receive a topical adhesive to thereby adhere to the skin and form a microbial barrier over the wound, wherein the wound closure patch defines a channel, wherein the wound closure patch comprises:

(i) a top-most surface, (ii) a bottom surface defining at least one opening in fluid communication with the channel, wherein the channel is interposed between the top-most surface and the bottom surface, (iii) a fluid coupling section in fluid communication with the channel, wherein the fluid coupling section is configured to couple with the cannula to thereby establish fluid communication between the cannula, the channel, and the at least one opening defined by the bottom surface, and (iv) at least one topical adhesive receiving pore fluidly independent from the channel, wherein the at least one topical adhesive receiving pore extends from the top-most surface to the bottom surface, wherein the channel and the at least one opening are fluidly isolated from the top-most surface.

2. The apparatus of claim 1, wherein the fluid coupling section further comprises a sealed fluid coupling section.

3. The apparatus of claim 1, wherein at least two topical adhesive receiving pores extend from the top-most surface to the bottom surface.

4. The apparatus of claim 1, wherein the wound closure patch extends from a first end toward a second end.

5. The apparatus of claim 4, wherein the fluid coupling section is located at the first end of the wound closure patch.

6. The apparatus of claim 5, wherein the channel extends longitudinally from the first end toward the second end.

7. The apparatus of claim 1, wherein the top surface comprises a blister pack filled with an agent.

8. The apparatus of claim 7, wherein the blister pack is configured to rupture to thereby distribute the agent into the channel.

9. The apparatus of claim 8, wherein the agent comprises a therapeutic fluid.

10. The apparatus of claim 1, wherein the wound closure patch further comprises at least one atraumatic nozzle in fluid communication with a respective opening of the at least one opening.

11. The apparatus of claim 10, wherein the at least one atraumatic nozzle extends downward from the bottom surface of the wound closure patch.

12. The apparatus of claim 1, further comprising a second cannula, wherein the wound closure patch comprises a second fluid coupling section in fluid communication with the channel and the second cannula.

13. The apparatus of claim 12, wherein the second cannula is configured to establish fluid communication with a fluid reservoir.

14. The apparatus of claim 1, further comprising a suctions distribution member configured to abut against the bottom surface of the wound closure patch such that the suction distribution member is interposed between the skin and the wound closure patch.

15. An apparatus, comprising:

(a) a cannula configured to establish fluid communication with a suction source; and (b) a wound closure patch dimensioned to cover a wound in skin, wherein the wound closure patch is configured to receive a topical adhesive via at least one topical adhesive receiving pore to thereby adhere to the skin and form a microbial barrier over the wound, wherein the wound closure patch comprises a bottom surface defining a plurality of openings, wherein the wound closure patch defines a longitudinally extending channel in fluid communication with the cannula such that the cannula is configured to induce suction through the plurality of openings via the longitudinally extending channel, wherein the at least one topical adhesive receiving pore is fluidly independent of the longitudinally extending channel, and wherein the at least one topical adhesive receiving pore extends from a top-most surface of the wound closure patch to the bottom surface, wherein the channel and the plurality of openings are fluidly isolated from the top-most surface.

16. The apparatus of claim 15, wherein the apparatus further comprises a suction distribution member configured to attach to the bottom surface of the wound closure patch.

17. The apparatus of claim 15, wherein the wound closure patch further comprises a plurality of atraumatic nozzles in fluid communication with a respective opening of the plurality of openings.

18. The apparatus of claim 15, wherein at least two topical adhesive receiving pores extend from the top-most surface to the bottom surface.

19. An apparatus, comprising:

(a) a wound closure patch dimensioned to cover a wound in skin, wherein the wound closure patch is configured to receive a topical adhesive via at least one topical adhesive receiving pore to thereby adhere to the skin and form a microbial barrier over the wound, wherein the wound closure patch comprises a bottom surface defining a plurality of openings, wherein the wound closure patch defines a longitudinally extending channel in fluid communication with the plurality of openings and fluidly independent of the at least one topical adhesive receiving pore, wherein the at least one topical adhesive receiving pore extends from a top-most surface of the wound closure patch to the bottom surface; and (b) a suction distribution member configured to attach to the bottom surface of the wound closure patch, wherein the channel and the plurality of openings are fluidly isolated from the top-most surface.

20. The apparatus of claim 19, wherein the suction distribution member comprises an open cell sponge material.

* * * * *